United States Patent [19]
Küfner-Mühl et al.

[11] Patent Number: 5,641,784
[45] Date of Patent: Jun. 24, 1997

[54] 8-SUBSTITUTED 1,3-DIALIPHATICXANTHINE DERIVATIVES

[75] Inventors: Ulrike Küfner-Mühl, Ingelheim; Werner Stransky, Gau-Algesheim; Gerhard Walther, deceased, late of Bingen, by Ruth Walther, heir; Karl-Heinz Weber, Gau-Algesheim; Helmut Ensinger, Ingelheim am Rhein; Franz Josef Kuhn, Gau-Algesheim; Günter Schingnitz, Bad Kreuznach; Erich Lehr, Waldalgesheim, all of Germany

[73] Assignee: Boehringer Ingelheim KG, Ingelheim am Rhein, Germany

[21] Appl. No.: 362,105

[22] Filed: Dec. 22, 1994

Related U.S. Application Data

[63] Continuation of Ser. No. 168,280, Dec. 15, 1993, abandoned, which is a continuation of Ser. No. 834,550, filed as PCT/EP91/01131, Jun. 19, 1991, abandoned.

[30] Foreign Application Priority Data

Jun. 22, 1990 [DE] Germany .................. 40 19 892.8

[51] Int. Cl.⁶ .................. C07D 473/00; A61K 31/52
[52] U.S. Cl. .................. 514/263; 544/272; 544/267
[58] Field of Search .................. 544/268, 272, 544/267; 514/263

[56] References Cited

U.S. PATENT DOCUMENTS

| | | | |
|---|---|---|---|
| 4,061,753 | 12/1977 | Bodor et al. | 424/253 |
| 4,548,820 | 10/1985 | Regnier et al. | 544/269 |
| 4,612,315 | 9/1986 | Jacobson et al. | 544/269 |
| 4,755,517 | 7/1988 | Bruns et al. | 514/263 |
| 4,833,146 | 5/1989 | Gebert et al. | 514/263 |
| 5,068,236 | 11/1991 | Suzuki et al. | 544/267 |
| 5,290,782 | 3/1994 | Susuki et al. | 514/263 |
| 5,525,607 | 6/1996 | Susuki et al. | 514/263 |
| 5,532,368 | 7/1996 | Küfner-Mühl et al. | 544/267 |

*Primary Examiner*—Robert T. Bond
*Assistant Examiner*—Pavanaram K. Sripada
*Attorney, Agent, or Firm*—Robert P. Raymond; Wendy E. Rieder; Mary-Ellen M. Devlin

[57] ABSTRACT

New xanthine compounds of formula I:

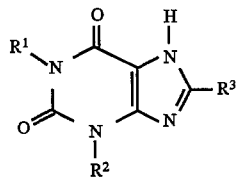

wherein the substituents are defined herein, which xanthines are useful as adenosine antagonists.

11 Claims, No Drawings

8-SUBSTITUTED 1,3-DIALIPHATICXANTHINE DERIVATIVES

This application is a continuation of prior U.S. application Ser. No. 08/168,280, filed Dec. 15, 1993, now abandoned, which is a continuation of prior U.S. application Ser. No. 07/834,550, filed as PCT/EP91/01131, Jun. 19, 1991, which is now abandoned.

The invention relates to new xanthine derivatives, processes for preparing them and their use as pharmaceutical compositions.

The new compounds correspond to general formula I

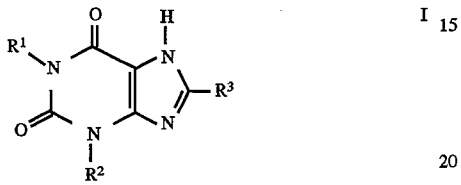

wherein $R^1$ represents a $C_{1-6}$-alkyl, preferably $C_{1-4}$-alkyl, a $C_{3-4}$-alkenyl or a $C_{3-4}$-alkynyl;

$R^2$ represents a $C_{1-6}$-alkyl, preferably $C_{1-4}$-alkyl, a $C_{3-4}$-alkenyl or a $C_{3-4}$-alkynyl;

$R^3$ represents an N-linked, optionally substituted, saturated or unsaturated 5-, 6- or 7-membered nitrogen-containing heterocyclic group which may contain as further heteroatoms oxygen, sulphur and/or a substituted nitrogen, preferably N-$C_{1-4}$-alkyl, whilst the heterocyclic group may carry one of the following groups, $C_{1-6}$, preferably $C_{1-4}$-alkyl, $OR^4$, $OR^7$; =O, —(CH$_2$)$_{1-4}$OR$^4$, —(CH$_2$)$_{1-4}$OR$^7$;

$R^3$ represents a monosaccharide, preferably a group of the formula

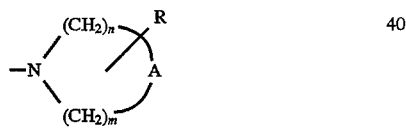

wherein
R=H, alkyl, $OR^4$, $OR^7$, $CH_2OR^4$, $CH_2OR^7$, =O
A=O, S, $CH_2$, N-$C_{1-6}$-alkyl,
n, m=1, 2, 3, 4 and n+m=3, 4, 5,
optionally substituted tetrahydrofuran or tetrahydropyran ring having one, preferably several radicals from the group $OR^4$, preferably OH, $OR^7$, $(CH_2)_{1-4}OR^4$ or $(CH_2)_{1-4}OR^7$, preferably $CH_2OH$;

$R^3$ represents an optionally substituted $C_{4-8}$, preferably $C_5$ or $C_6$-cycloalkane, cycloalkanone or cycloalkanol group, optionally mono- or polysubstituted by
$C_{1-6}$, preferably $C_{1-4}$-alkyl, $C_{3-6}$, preferably $C_3$ or $C_4$-alkenyl, $C_{3-6}$, preferably $C_3$ or $C_4$-alkynyl, $C_{1-4}$-alkylidene, phenyl, substituted phenyl, optionally substituted aralkyl, $NR^5R^6$, $COOR^4$, $CONR^5R^6$, $OR^4$, $SR^4$, $OR^7$, —(CH$_2$)$_{1-4}CONR^5R^6$, $C_{1-4}$-alkyl-S-R$^4$, $C_{1-4}$-alkyl-OR$^4$, preferably $CH_2OR^4$, $C_{1-4}$-alkyl-OR$^7$, preferably $CH_2OR^7$, $C_{1-4}$-alkyl-COOR$^4$, preferably $CH_2$-COOR$^4$, —(CH$_2$)$_{1-4}$-NR$^5R^6$, NHR$^7$, —(CH$_2$)$_{1-4}$-NHR$^7$, preferably NHCO-$C_{1-6}$-alkyl, and/or optionally substituted $C_{3-6}$-cycloalkyl;

$R_3$ represents a ketal of general formula

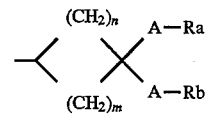

wherein

A represents oxygen or sulphur, m, n=0, 1, 2, 3, 4, 5 or 6, m+n=2, 3, 4, 5 or 6, $R^a$ may represent $C_{1-4}$-alkyl, $R^b$ may represent $C_{1-4}$-alkyl, or $R^a$ and $R^b$ together form a $C_2$ or $C_3$-alkylene bridge which may optionally be mono- or disubstituted by $C_{1-5}$-alkyl, $C_{1-5}$-alkyloxycarbonyl or hydroxy-$C_{1-5}$-alkyl, preferably hydroxymethyl, whilst the carbocyclic ring of the ketal may be substituted by one or more of the following groups:

$C_{1-6}$, preferably $C_{1-4}$-alkyl, $C_{3-6}$, preferably $C_3$ or $C_4$-alkenyl, $C_{3-6}$, preferably $C_3$ or $C_4$-alkynyl, $C_{1-4}$-alkylidene, phenyl, substituted phenyl, optionally substituted aralkyl, $NR^5R^6$, $COOR^4$, $CONR^5R^6$, $OR^4$, $SR^4$, $OR^7$, —(CH$_2$)$_{1-4}CONR^5R^6$, $C_{1-4}$-alkyl-S-R$^4$, $C_{1-4}$-alkyl-OR$^4$, preferably $CH_2$-OR$^4$, $C_{1-4}$-alkyl-OR$^7$, preferably $CH_2OR^7$, $C_{1-4}$-alkyl-COOR$^4$, preferably $CH_2$-COOR$^4$, —(CH$_2$)$_{1-4}$-NR$^5R^6$, NHR$^7$, —(CH$_2$)$_{1-4}$-NHR$^7$, preferably NHCO-$C_{1-6}$-alkyl, optionally substituted $C_{3-6}$-cycloalkyl;

$R^3$ represents a group of general formula

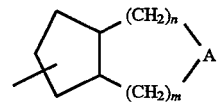

wherein

A=$CH_2$, O, S; n, m=0, 1, 2, 3 or 4 and n+m=2, 3 or 4 and one of the two rings may be mono- or polysubstituted by $OR^4$, $C_{1-6}$, preferably $C_{1-4}$-alkyl, $C_{3-6}$, preferably $C_3$ or $C_4$-alkenyl, $C_{3-6}$, preferably $C_3$ or $C_4$-alkynyl, $C_{1-4}$-alkylidene, phenyl, substituted phenyl, optionally substituted aralkyl, $NR^5R^6$, $COOR^4$, $CONR^5R^6$, $OR^4$, $SR^4$, $OR^7$, —(CH$_2$)$_{1-4}$-NR$^5R^6$, —(CH$_2$)$_{1-4}CONR_5R_6$, $C_{1-4}$-alkyl-S-R$^4$, $C_{1-4}$-alkyl-OR$^4$, =O, preferably $CH_2OR^4$, $C_{1-4}$-alkyl-OR$^7$, preferably $CH_2OR^7$, $C_{1-4}$-alkyl-COOR$^4$, preferably $CH_2$—COOR$^4$, NHR$^7$, preferably NHCO-$C_{1-6}$-alkyl, optionally substituted $C_{3-6}$-cycloalkyl;

$R^3$ represents a group of general formula

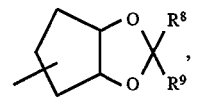,

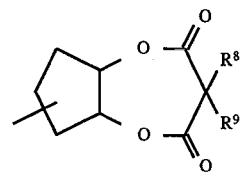

$R^3$ represents a group of the formula

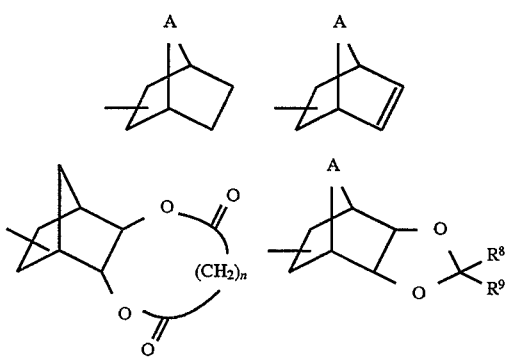

n=1, 2, 3

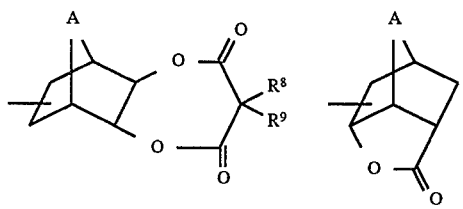

with A=O, CH$_2$, —CH$_2$—CH$_2$—, whilst the ring system is optionally substituted by one or more $C_{1-6}$, preferably $C_{1-4}$-alkyl, $C_{2-6}$, preferably $C_2$ and $C_3$-alkenyl, $C_{2-6}$, preferably $C_2$ and $C_3$-alkynyl, $NR^5R^6$, $COOR^4$, $CONR^5R^6$, $OR^4$, $OR^7$, $SR^4$, =O, CH$_2$OR$^7$, CH$_2$COOR$^4$, CH$_2$CONR$^5R^6$;

$R^3$ preferably represents a group of general formula

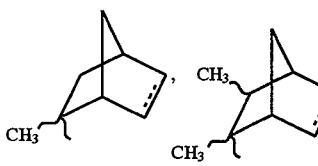

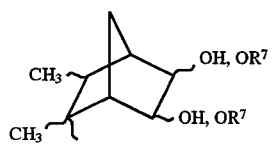

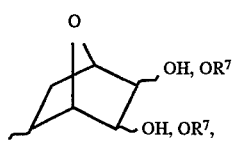

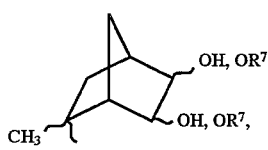

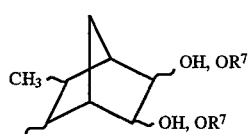

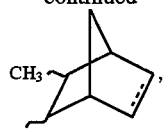

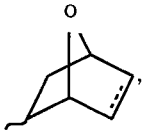

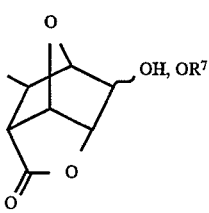

$R^4$ represents hydrogen, $C_{1-8}$, preferably $C_{1-4}$-alkyl, optionally substituted $C_{3-6}$-cycloalkyl, optionally substituted $C_{1-4}$-alkylphenyl, $C_{3-6}$, preferably $C_3$ or $C_4$-alkenyl, optionally substituted aralkyl;

$R^5$ represents hydrogen, $C_{1-6}$, preferably $C_{1-4}$-alkyl, optionally substituted $C_{3-6}$-cycloalkyl, optionally substituted aralkyl;

$R^6$ represents hydrogen, a $C_{1-6}$, preferably $C_{1-4}$-alkyl group, optionally substituted aralkyl, preferably an optionally substituted benzyl group, a group o: general formula —(CH$_2$)$_n$—NR$^5R^5$ (where $R^5$ may be the same or different), —(CH$_2$)$_n$—CN, —(CH$_2$)$_n$—OR$^4$, —(CH$_2$)$_n$—OR$^7$, —(CH$_2$)$_n$—NHR$^7$ where n=2, 3, 4, 5, 6, or 8, or $R^5$ and $R^6$ together form an optionally substituted, preferably $C_{1-4}$-alkyl-substituted, five-, six- or seven-membered ring which may contain a further heteroatom from the group comprising oxygen, sulphur or nitrogen, whilst the nitrogen atom may be substituted by the group $R^4$;

$R^7$ represents an amino acid group, linked via the carbonyl function, of a naturally occurring amino acid, CO—$C_{1-13}$-alkyl, preferably CO—$C_{2-4}$-alkyl, optionally substituted CO—$C_{1-13}$-alkylphenyl;

$R^8$ represents hydrogen, $C_{1-6}$, preferably $C_{1-4}$-alkyl, optionally substituted $C_{3-6}$-cycloalkyl, optionally substituted aralkyl;

$R^9$ represents hydrogen, $C_{1-6}$, preferably $C_{1-4}$-alkyl, optionally substituted $C_{3-6}$-cycloalkyl, optionally substituted aralkyl;

or $R^8$ and $R^9$ form together with the CH$_2$ group an optionally substituted 5- or 6-membered carbocyclic ring, in the form of a racemate, an optically active compound, a pure diastereomer or mixture of diastereomers and optionally the pharmacologically acceptable acid addition salts thereof.

Preferred compounds of general formula I are those wherein $R^1$ represents a $C_{3-6}$-alkyl group, a propenyl group or propargyl group;

$R^2$ represents a $C_{3-4}$-alkyl group, a propenyl group or a propargyl group;

$R^3$ represents an N-linked saturated 5- or 6-membered ring which may optionally contain oxygen or sulphur as a further heteroatom, preferably selected from the group comprising pyrrolidine, piperidine, morpholine, thiomorpholine, pyrrolidinone, which may carry one or more of the following groups $C_{1-4}$-alkyl, $OR^4$, $OR^7$, =O;

$R^3$ represents a 2,3,4-trihydroxy-tetrahydrofuran-5-yl, a 2,3,4,5-tetrahydroxy-tetrahydropyran-6-yl, a 2-hydroxymethyl-3,4,5-trihydroxy-tetrahydropyran-6-yl, $R^3$ represents a cyclopentane or cyclohexane or cyclopentanone or cyclopentanol or cyclohexanone or cyclohexanol or an ethylene ketal of cyclopentanone or cyclohexanone which may be mono- or polysubstituted by $C_{1-4}$-alkyl, $C_{3-4}$-alkenyl, $C_{3-4}$-alkynyl, $C_{1-3}$-alkylidene, optionally substituted phenyl, $OR^4$, $OR^7$, $CH_2$—$COOR^4$, $CH_2OR^7$, $NR^5R^6$, $COOR^4$, $CONR^5R^6$, $NHR^7$, $CH_2OR^4$, whilst $R^4$ may represent hydrogen, methyl, ethyl or propyl;

$R^3$ represents norbornane or norbornene, 7-oxabicyclo[2.2.1]heptane or heptene, 3-oxo-2,7-dioxatricyclo[4.2.1.0$^{4.8}$]nonane, optionally substituted by $CH_3$, $OR^4$, $OR^7$;

$R^3$ represents a bicyclo[3.3.0]octane or oxa- or thiabicyclo[3.3.0]octane, optionally substituted by $OR^4$, =O, $OR^7$;

$R^4$ represents hydrogen, a $C_{1-3}$-alkyl group, benzyl, $R^5$ represents hydrogen, a $C_{1-3}$-alkyl group;

$R^6$ represents hydrogen, methyl, ethyl, propyl, —$(CH_2)_nNH_2$, $(CH_2)_n$—CN, $(CH_2)_n$—$OR^4$, $(CH_2)_n$—$OR^7$, $(CH_2)_nNR^5R^5$, $(CH_2)_nNHR^7$, (n=2–8);

$R_7$ represents prolinoyl, CO—$(CH_2)_{0-3}$—$CH_3$ or benzoyl, and optionally the optically active compounds thereof as well as the acid addition salts thereof.

Alkyl, alkenyl or alkynyl groups may be straight-chained or branched. Examples of alkyl groups, including those which are components of other substituents, are methyl, ethyl, propyl, isopropyl, butyl, sec.-butyl, isobutyl, tert.-butyl, pentyl, isopentyl, neo-pentyl, hexyl or isohexyl and examples of longer-chained alkyl groups are decanyl, undecanyl, dodecanyl and tridecanyl and the isomers thereof. Examples of alkenyl groups include allyl (provided that it does not form any enamines), propenyl, isopropenyl, butenyl and isobutenyl. (Et=ethyl).

Alkyl, alkenyl and alkynyl groups, as defined according to the invention, may be mono- or polysubstituted. Examples of suitable substituents include hydroxy, halogen (fluorine, chlorine, bromine or iodine), nitro, cyano, amino, $C_{1-4}$-alkylamino or $C_{1-4}$-dialkylamino, SH, S-$C_{1-4}$-alkyl and cyclopropyl.

Examples of substituted alkyl groups include $CF_3$, hydroxymethyl, hydroxyethyl, cyanomethyl, benzyl, ethylphenyl, cyclopropylmethyl and cyclopropylethyl.

Examples of cycloalkyl groups include, for example, cyclopropyl, cyclobutyl, cyclopentyl and cyclohexyl, which may be substituted by $C_{1-4}$-alkyl or halogen. The term aryl denotes an aromatic cyclic system having up to 10, preferably 6 to 10 carbon atoms which may optionally contain as a heteroatom oxygen, sulphur or nitrogen and which may optionally be substituted by $C_{1-4}$-alkyl, halogen, hydroxy, nitro, $C_{1-4}$-alkoxy, amino, $C_{1-4}$-alkylamino and/or $C_{1-4}$-dialkylamino, the preferred aryl group being phenyl. A benzyl group, like a phenyl group, may be mono- or polysubstituted by $C_{1-4}$-alkyl, preferably methyl, by $C_{1-4}$-alkoxy, preferably methoxy, hydroxy and/or halogen, such as fluorine, chlorine or bromine, trifluoromethyl, halogen—preferably chlorine or bromine, CN, $NO_2$, cyano, COH, COOH, $COOC_{1-4}$-alkyl, $CONH_2$, $CON(C_{1-4}$-alkyl$)_2$, cyclopropyl, amino, $C_{1-4}$-alkylamino, $C_{1-4}$-dialkylamino, hydroxymethyl, $SO_2$-$C_{1-4}$-alkyl, $SO_2$-$C_{1-4}$, hydroxyalkyl, hydroxy, SH, S-$C_{1-4}$-alkyl.

Aralkyl represents an aryl group linked by $C_{1-6}$, preferably phenyl.

Examples of substituted phenyl are as follows: 3-chlorophenyl, 4-chlorophenyl, 3-bromophenyl, 4-bromophenyl, 4-fluoromethyl, 2-chlorophenyl, 2-bromophenyl, 3-fluorophenyl, 2,3-dichlorophenyl, 2-methylphenyl, 4-methylphenyl, 3-ethylphenyl, 4-propylphenyl, 4-isopropylphenyl, 4-butylphenyl, 4-tert-butylphenyl, 4-iso-butylphenyl, 4-pentylphenyl, 2,4-dimethylphenyl, 2-trifluoromethylphenyl, 3-trifluoromethylphenyl, 4-trifluoromethylphenyl, 2-methoxyphenyl, 4-methoxyphenyl, 3-ethoxyphenyl, 2-propoxyphenyl, 4-butoxyphenyl, 2,4-dimethoxyphenyl, 3,4,5-trimethoxyphenyl, 2-chlorobenzyl, 2,3-dichlorobenzyl, 2-methylbenzyl, 2-trifluoromethylbenzyl, 4-methoxy-benzyl, 3,4,5-trimethoxybenzyl, 2-(2-chlorophenyl)ethyl.

Examples of cyclic groups of general formula $NR^5R^6$ include: pyrrole, pyrroline, pyrrolidine, 2-methylpyrrolidine, 3-methylpyrrolidine, piperidine—optionally mono- or polysubstituted by $C_{1-4}$-alkyl-piperazine, N-methylpiperazine, N-ethylpiperazine, N-(n-propyl)-piperazine, N-benzylpiperazine, morpholine, thiomorpholine, imidazole, imidazoline, imidazolidine, pyrazole, pyrazoline, pyrazolidine, whilst the above-mentioned heterocyclic groups may be substituted by $C_{1-4}$-alkyl, preferably methyl.

Examples of heterocyclic groups which may be linked via a carbon atom include tetrahydrofuran, 2-methyltetrahydrofuran, 2-hydroxymethylfuran, tetrahydrofuranone, γ-butyrolactone, α-pyran, γ-pyran, tetrahydropyran, whilst the heterocyclic group may be substituted as given in the definitions.

Examples of heterocyclic groups which may be linked via an N-atom and contain a nitrogen atom include: pyrrolidine, piperidine, morpholine, thiomorpholine, pyrrolidinone, whilst the above-mentioned heterocyclic groups may also be substituted by $C_{1-4}$-alkyl, $C_{1-4}$-alkoxy, $OR_4$ or =O.

Examples of naturally occurring amino acids include alanine, valine, leucine, isoleucine, proline, phenylalanine, tryptophan, methionine, glycine, serine, threonine, cysteine, tyrosine, asparagine, glutamine, histidine, arginine, lysine.

For the definition of monosaccharides reference is made to "Beyer, Lehrbuch der organischen Chemie, 21st Edition".

The definition —$(CH_2)_{1-4}$ also includes branched bridge members such as —$CH_2$—$CH(CH_3)$—$CH_2$— whilst "O" represents an oxygen atom linked via a double bond.

Xanthines of similar structure, which must be partly disclaimed, are known from European Patent Application 374 808, which was not a prior publication. The compounds according to the invention are adenosine antagonists; they have a particularly strong affinity for the $A_1$-receptor and a high selectivity for this receptor subtype. Thus, for example, 8-(3.4-cis-dihydroxycyclopentyl)-1,3-dipropyl-7H-purine-2,6-dione has an $A_1$-receptor affinity of $K_i$=14 nMol and 8-(7-oxo-cis-bicyclo[3.3.0]octan-3-yl)-1,3-dipropyl-7H-purine-2,6-dione (Example 14) has a value of 3.9 nMol.

In hippocampus sections the substances antagonise the adenosine-induced suppression of the total peak after electrical stimulation. In vivo, an increased acetylcholine content can be found in rats' brains.

These results indicate that the xanthine derivatives described intensify the natural cell activity of cholinergic neurones in the brain and thus turn out to be functional cholinomimetics with a central effect. EEG investigations on cats show a significant increase in vigilance.

Substances of this kind are of great interest for the symptomatic therapy of degenerative disorders of the central nervous system such as senile dementia and Alzheimer's disease.

The high receptor affinity should make it possible to treat patients with low doses, so that hardly any side effects can be expected which are not due to the blockade of adenosine receptors. Similarly, $A_2$-dependent side effects should be ruled out because of the high $A_1$-selectivity of the compounds. In addition to being us as gerontopsycho drugs and nootropics the adenosine antagonists described may be useful in treating cardiac and circulatory disorders.

Other possible indications are degenerative disorders such as organic brain syndrome, Parkinson, traumatic CNS-damage, post stroke neurological deficit, respiratory depression (intoxication, post op), early childhood brain trauma, dyslexia. The substances would also be suitable for treating neurological deficits, e.g. after traumatic brain injury, or after stroke.

The pharmacological results are based on the methods of investigation recited in the references from the literature which follow.

Lohse M. J., V. Lenschow and U. Schwabe (1984) Mol. Pharmacol. 26, 1–9 (1984);

Virus, M. R., T. Baglajewski and M. Radulovacki (1984) Neurobiology of Ageing 5, 61–62;

Daly, J. W., W. Padgett, M. T. Shamin, P. Butts-Lamb J. Waters (1985) J. Med. Chem. 28, 487–492 (1985);

Bruns, R. F., G. H. Lu and T. A. Pugsley (1986) Mol. Pharmacol. 29, 331–346

The compounds according to the invention may be prepared by analogous methods known per se.

Preparation of the compounds

Generally, 8-substituted 1,3-dialkylxanthines are obtained by reacting 1,3-dialkyl-5,6-diaminouracils with aldehydes or carboxylic acids or by reacting 1,3-dialkyl-6-amino-5-nitrosouracils with aldehydes in the presence of dimethylhydrazine.

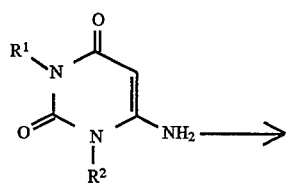

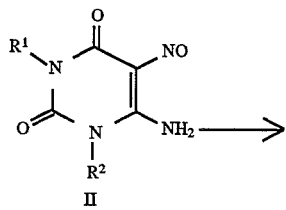

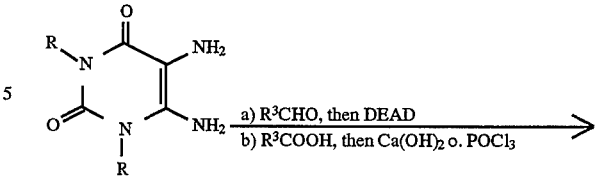

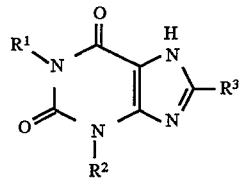

5,6-Diamino-1,3-dimethyluracil is commercially available; derivatives substituted with other groups are prepared by reacting the corresponding dialkylurea with cyanoacetic acid, followed by nitrosation and optionally hydrogenation or reduction with dithionite to obtain the diamine (J. Org. Chem. 16, 1879 (1951) and Can. J. Chem. 46, 3413 (1968)).

All the carboxylic acids or aldehydes which are needed to react with the 5,6-diamino-1,3-dialkyluracils can be obtained commercially, prepared by methods known from the literature or synthesised by simple methods known to any chemist from precursors known from the literature. Individual examples are given in the following paragraphs. Other methods of synthesis are described in European Patent Application 374 808, to which reference is made here.

1)

Tetrahydrofurans or tetrahydropyrans polysubstituted with hydroxy, alkoxy or acyloxy groups, as the groups $R^3$, are obtained from suitable carbohydrate derivatives in which the primary hydroxy group is tritylated by conventional methods and the remaining alcohol functions are alkylated. Acid hydrolysis of the tritylether and oxidation of the alcohol, e.g. with pyridinium dichromate in dimethylformamide, leads to the corresponding carboxylic acid which may be used in the xanthine synthesis in accordance with the general rules. If benzyl groups are used in the alkylation, these may be removed from the finished xanthine by hydrogenolysis and the free hydroxy functions acylated.

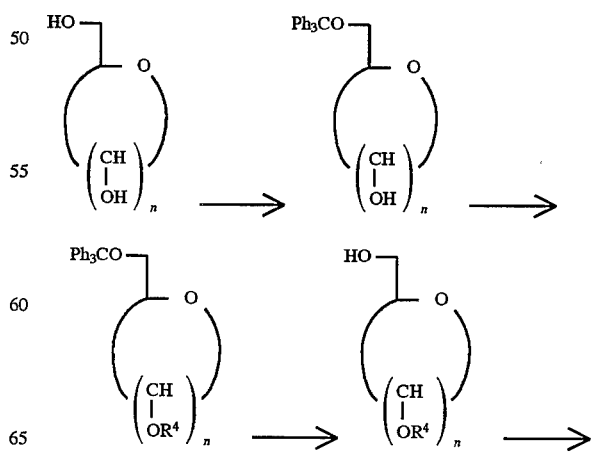

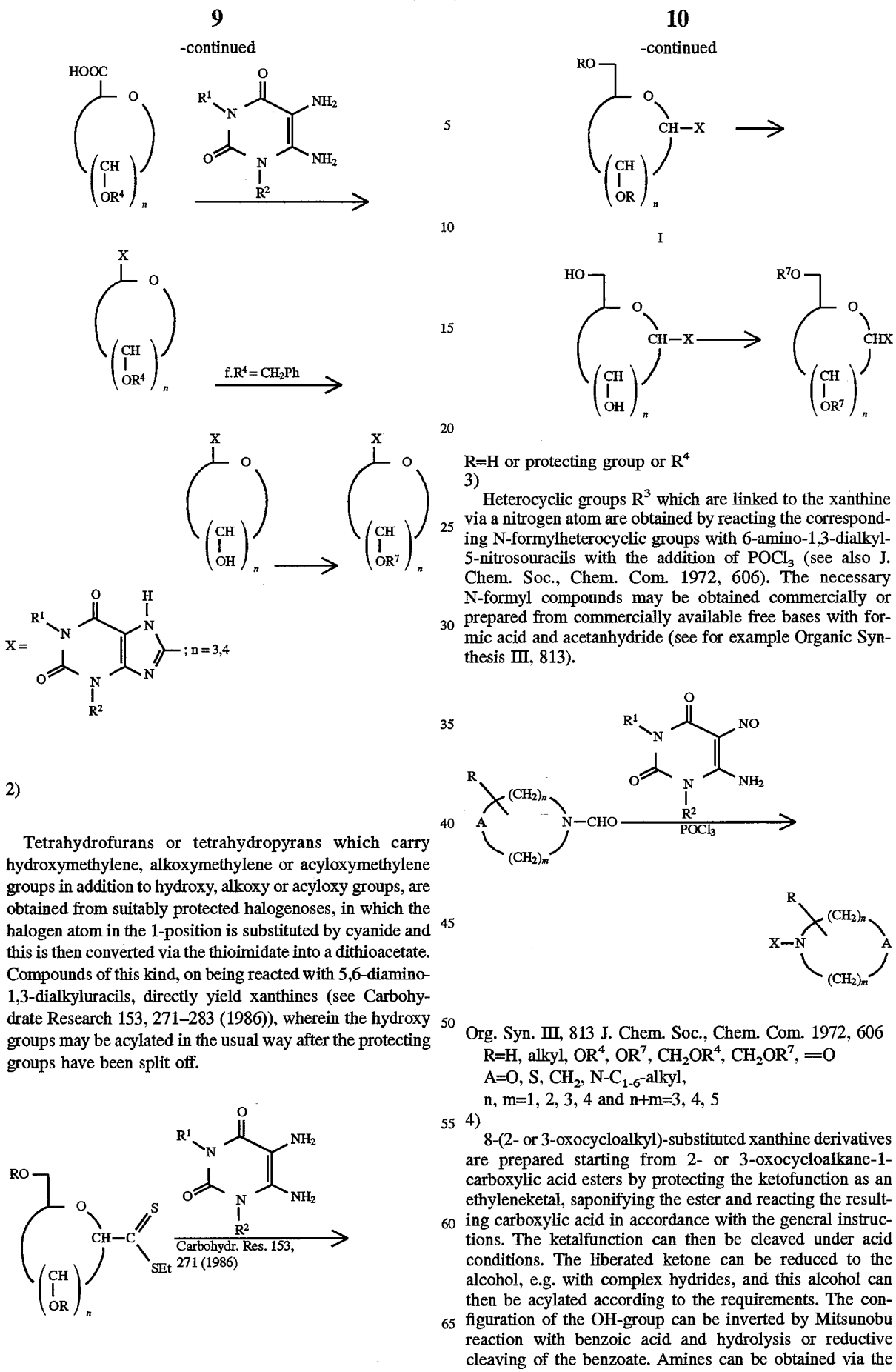

R=H or protecting group or $R^4$

3)

Heterocyclic groups $R^3$ which are linked to the xanthine via a nitrogen atom are obtained by reacting the corresponding N-formylheterocyclic groups with 6-amino-1,3-dialkyl-5-nitrosouracils with the addition of $POCl_3$ (see also J. Chem. Soc., Chem. Com. 1972, 606). The necessary N-formyl compounds may be obtained commercially or prepared from commercially available free bases with formic acid and acetanhydride (see for example Organic Synthesis III, 813).

Org. Syn. III, 813 J. Chem. Soc., Chem. Com. 1972, 606
R=H, alkyl, $OR^4$, $OR^7$, $CH_2OR^4$, $CH_2OR^7$, =O
A=O, S, $CH_2$, $N-C_{1-6}$-alkyl,
n, m=1, 2, 3, 4 and n+m=3, 4, 5

4)

8-(2- or 3-oxocycloalkyl)-substituted xanthine derivatives are prepared starting from 2- or 3-oxocycloalkane-1-carboxylic acid esters by protecting the ketofunction as an ethyleneketal, saponifying the ester and reacting the resulting carboxylic acid in accordance with the general instructions. The ketalfunction can then be cleaved under acid conditions. The liberated ketone can be reduced to the alcohol, e.g. with complex hydrides, and this alcohol can then be acylated according to the requirements. The configuration of the OH-group can be inverted by Mitsunobu reaction with benzoic acid and hydrolysis or reductive cleaving of the benzoate. Amines can be obtained via the

2)

Tetrahydrofurans or tetrahydropyrans which carry hydroxymethylene, alkoxymethylene or acyloxymethylene groups in addition to hydroxy, alkoxy or acyloxy groups, are obtained from suitably protected halogenoses, in which the halogen atom in the 1-position is substituted by cyanide and this is then converted via the thioimidate into a dithioacetate. Compounds of this kind, on being reacted with 5,6-diamino-1,3-dialkyluracils, directly yield xanthines (see Carbohydrate Research 153, 271–283 (1986)), wherein the hydroxy groups may be acylated in the usual way after the protecting groups have been split off.

oxime by hydrogenation and then be alkylated or acylated. Moreover, after the 7-N-atom in the xanthine has been protected by benzylation, the ketones may be converted with the lithium salt of the 2-trimethylsilyl-1,3-dithiane into the ketenedithioacetal, from which carboxylic acid or ester functions can be released, e.g. by treating with mercury or copper salts (e.g. analogously to Tetrahedron Lett. 29, 1493 (1988) or J. Chem. Res. (S) 1989, 320). By reduction of the esters, primary alcohols are obtained which may be alkylated and acylated. When reacted with suitable amines the carboxylic acids yield the corresponding amide derivatives. The 7-N-benzyl group is split off again by hydrogenolysis after the functionalisation of the group in the 8-position is complete.

5)

2-Alkyl-3-oxocycloalkyl groups are introduced into the 8-position of the xanthines by reacting cycloalkenones [according to J. Org. Chem. 54, 5003 (1989)] with the lithium salt of the methoxyphenylthiotrimethylsilylmethane in the presence of the desired alkylhalide, desilylating the reaction product and producing the corresponding carboxylic acid by oxidative hydrolysis; this carboxylic acid is reacted according to the general procedure and the ketofunction can then be subjected to various subsequent reaction as described in paragraph 4.

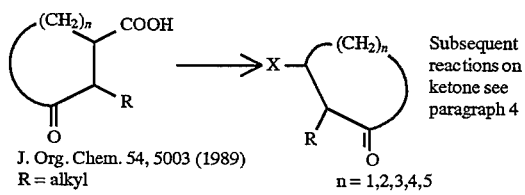

J. Org. Chem. 54, 5003 (1989)
R = alkyl
n = 1,2,3,4,5

A special case is the preparation of 2-methyl-3-oxo-5-(2-propenyl)carboxylic acid which is obtained from carvone, in accordance with Heterocycles 26, 1491 (1987). After xanthine has been reacted according to the general method, succeeding compounds are obtained by hydrogenation or hydroboration/oxidation of the double bond and/or by the method described in paragraph 4.

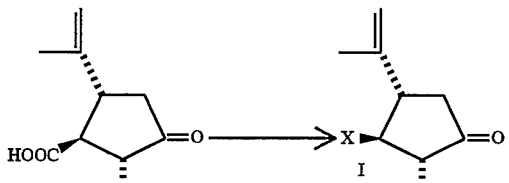

Heterocycles 26, 1491 (1987)

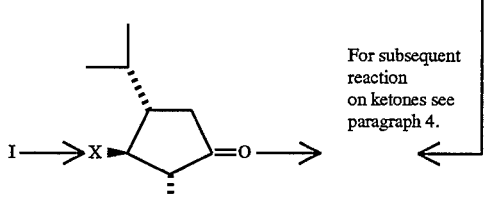

For subsequent reaction on ketones see paragraph 4.

6)

The carboxylic acids required for the synthesis of 8-(5-alkyl- or 5-aryl)-3-oxocyclopentylxanthine derivatives are prepared according to Liebigs Ann. Chem. 728, 21 (1969). Further functionalisation is carried out as described in paragraph 4.

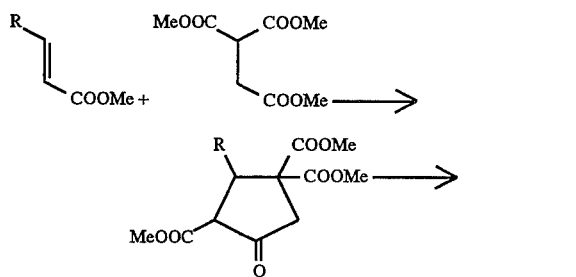

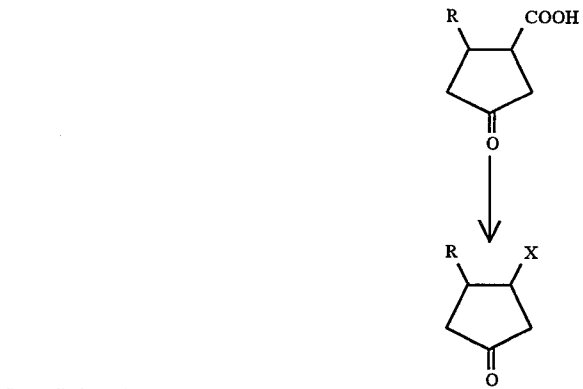

R = Alkyl, Aryl

Liebigs Ann. Chem. 728, 21 (1969)

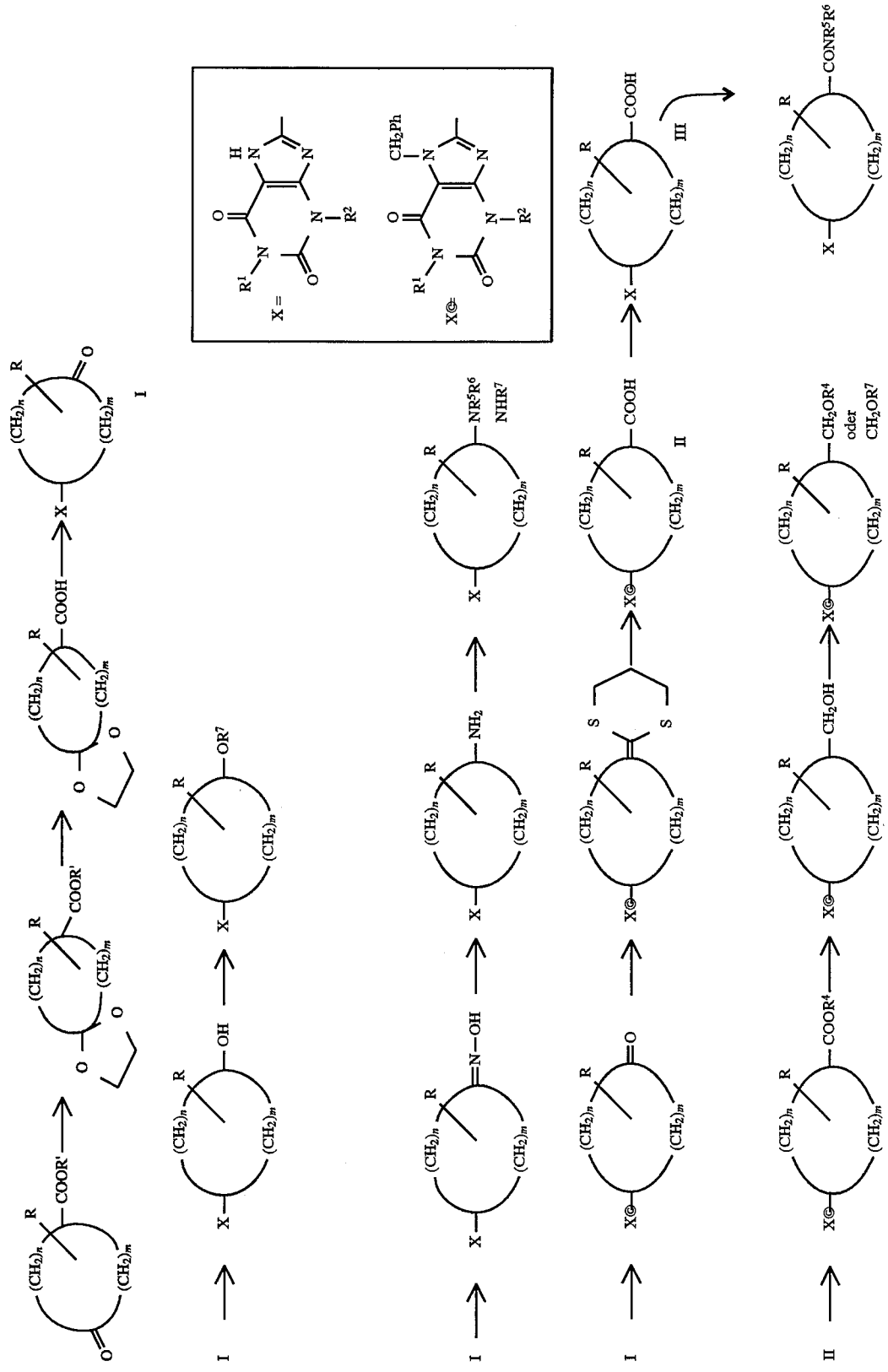

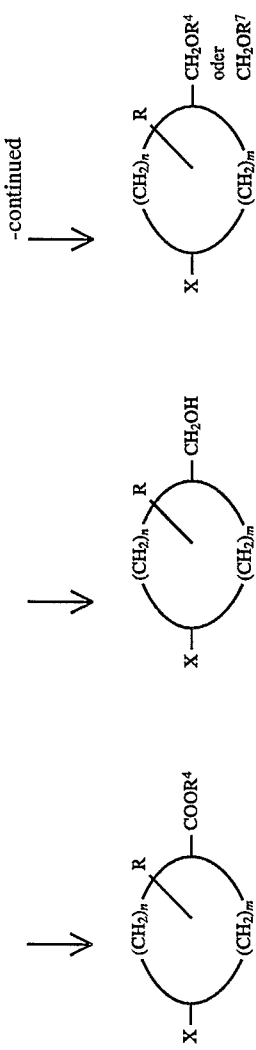

7)

In order to synthesise 1-alkyl-2-hydroxycycloalkane-1-carboxylic acids, 2-oxocycloalkanecarboxylic acid esters are used as starting materials, analogously to Helv. Chim. Acta 72, 690 (1989) which yield the required carboxylic acids in protected form after yeast reduction, cyclisation with t-butyraldehyde and alkylation. After the protecting group has been split off under acid conditions the hydroxy function is blocked with the t-butyldimethylsilyl protecting group and then the xanthine is synthesised by the general method. Desilylation with fluoride leads to the alcohol, which can be alkylated, acylated or oxidised to yield the ketone. This may be followed by further subsequent reactions as described in paragraph 4.

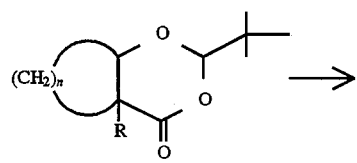

Helv. Chim. Acta 72, 690 (1989)

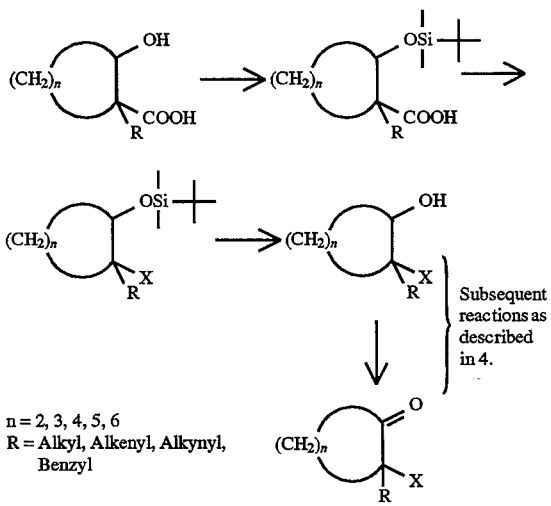

n = 2, 3, 4, 5, 6
R = Alkyl, Alkenyl, Alkynyl, Benzyl

8)

Cyclopentane or cyclohexane components polyfunctionalised with hydroxy, alkoxy or acyloxy group and possibly additional C-substituents can be prepared from carbohydrates in various ways. By way of example, mention may be made of J. Org. Chem. 54, 2268 (1989).

9)

1-Alkyl-2-alkyl- or 1-alkyl-2-arylcycloalkane-1-carboxylic acids are obtained by means of aldehydes which are prepared, analogously to Tetrahedron Lett. 30, 2465 (1985), from the t-leucine-t-butylester imines of the corresponding 1-cycloalkenecarboxaldehydes and may be reacted in accordance with the general procedure.

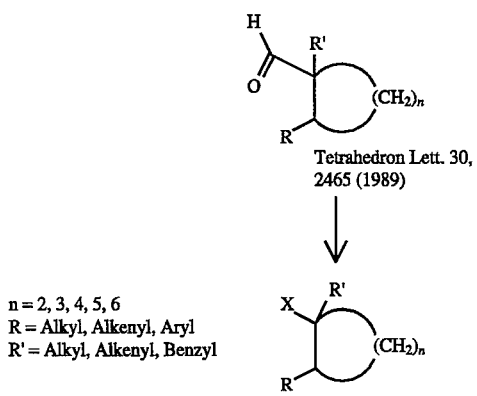

Tetrahedron Lett. 30, 2465 (1989)

n = 2, 3, 4, 5, 6
R = Alkyl, Alkenyl, Aryl
R' = Alkyl, Alkenyl, Benzyl

10)

Starting from 3-cyclopentene-1-carboxylic acid (J. Heterocycl. Chem. 26, 451 (1989)) the corresponding xanthine derivative is obtained, in accordance with the general procedure, wherein the double bond can be cis-hydroxylated by oxidation with N-methylmorpholine-N-oxide/osmium tetroxide or converted into the trans-diol by epoxidation with peracids and hydrolysis of the epoxide. The hydroxy groups can then be acylated; in the reaction with 1,n-dicarboxylic acid chlorides, cyclic diesters are formed whilst reaction with ketones yields cyclic ketanes.

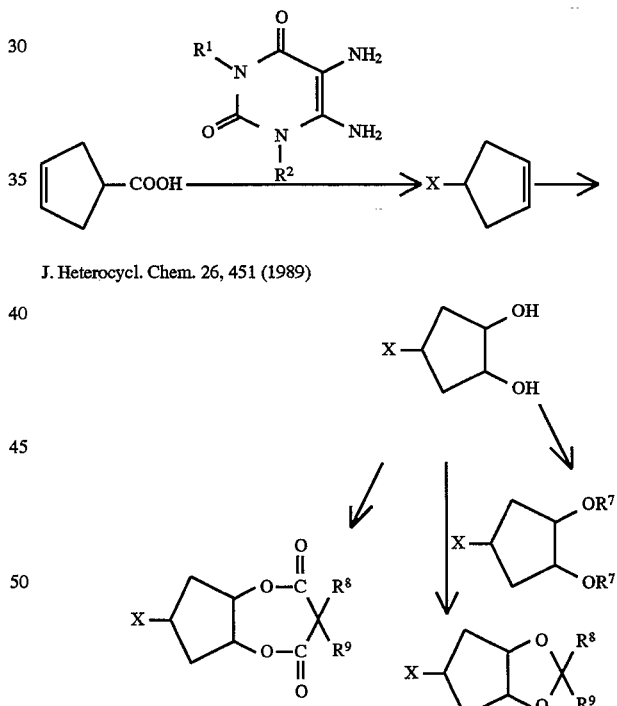

J. Heterocycl. Chem. 26, 451 (1989)

R, R'=H, alkyl, cycloalkl or $R^8$ and $R^9$ together with the ketal carbon atom form a 5- or 6-membered ring

11)

A hydroxyepoxide is obtained from cycloalkenones by DIBAH-reduction of the ketone to yield the alcohol and subsequent Sharpless epoxidation of the allyl alcohol. Subsequent epoxide opening with trimethylsilylcyanide, protection or alkylation of the hydroxy functions and saponification of the nitrile result in the corresponding carboxylic acid component which is reacted in accordance with general procedures to obtain the xanthine. After the protecting groups have been split off, the alcohol groups can be acylated again.

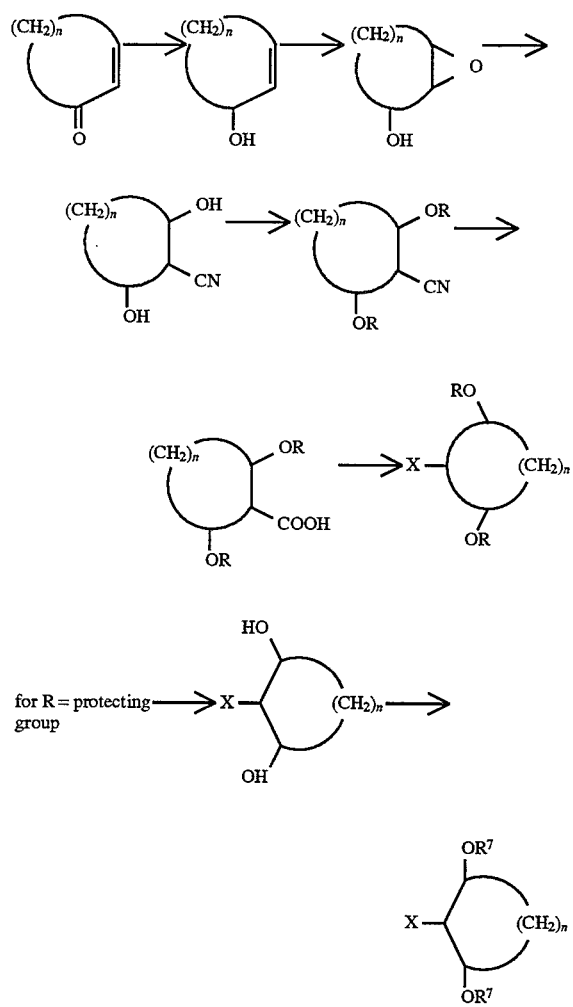

R=protecting group or $R^4$

12) Pulegonic acid (5-methyl-2-(2-propylidene)-1-cyclopentane-carboxylic acid) can be prepared by Favorski-rearrangement from pulegone dibromide (J. Org. Chem. 30, 41 (1964)) and reacted to yield the xanthine according to the general method. The double bond may be hydrogenated to form the propyl group or cleaved ozonolytically to yield the ketone, which may be subjected to the subsequent reactions described in paragraph 4.

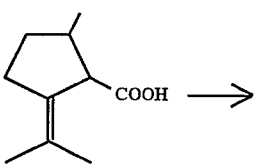

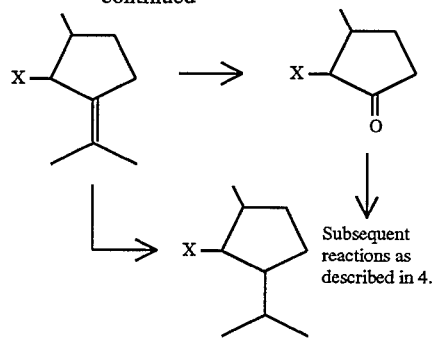

J. Org. Chem. 30, 41 (1964)

13)

1-Alkyl- or 1-arylcycloalkanecarboxylic acids may be obtained commercially or prepared by methods known from the literature, e.g. according to Liebigs Ann. Chem., 618, 251, 261, 264, 266 (1952) or Org. Synth. 46, 72 (1966), and converted into xanthines according to the general procedure. 2-alkylcycloalkanecarboxylic acids are synthesised, for example, according to Liebigs Ann. Chem. 491, 189, 207 (1931) or J. Am. Chem. Soc. 71, 81 (1949) or J. Chem. Soc. 1949, 1011; the 2,5-dialkyl-derivatives are obtained analogously to J. Am. Chem. Soc. 72, 256ff (1950); 2,3-dialkyl-1-cyclopentanecarboxylic acids are prepared according to Bull. Soc. Chim. Fr. 1958, 199ff.

14)

3-oxa- or 3-thiabicyclo[3.3.0]octane-7-carboxylic acid is obtained starting from the corresponding 7-oxo-compound (see Tetrahedron 40, 761 (1984) or J. Org. Chem. 114, 177 (1984)) by reacting with the lithium salt of 2-trimethylsilyl-1,3-dithiane to obtain the corresponding ketenedithioacetal and cleaving the acetal to obtain the carboxylic acid (see paragraph 4.). The xanthine derivatives are obtained in accordance with the general procedure.

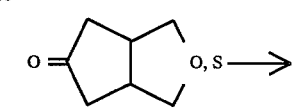

J. Org. Chem. 114, 177 (1984)

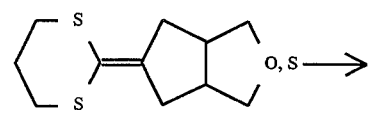

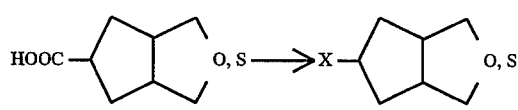

15)

Starting from bicyclo[3,3,0]octane-2,7-dione, the monothioketal is synthesised with 1,2-dimercaptoethane. The second ketofunction is converted, as described above, into the carboxylic acid which reacts according to the general procedure to form the xanthine. Subsequent reactions in the keto group may be carried out as described in paragraph 4. The isomers are separated by chromatography.

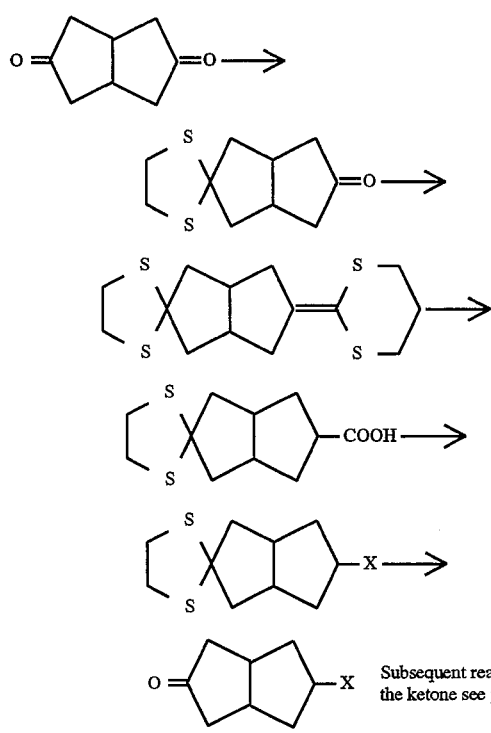

16)

The preparation of 2-ethoxycarbonyl-7,7-ethylenedioxybicyclo[3,3,0]octane-3-one is described in Tetrahedron Lett. 1978, 3743, Tetrahedron Lett. 1979, 433 and J. Chem. Soc., Chem. Commun. 1978, 1067. The ketalisation of the second keto-function as well, subsequent saponification of the ester and reaction analogously to the general procedure yields the corresponding xanthine derivative, the free keto groups of which may be obtained by acid hydrolysis. If, on the other hand, the keto group in the alpha-position relative to the ester is protected with 1,2-dimercaptoethane to yield the dithioketal, once the xanthine synthesis has been carried out analogously the two ketal protecting groups can be split off independently of each other (the ketal with acid, the thioketal by treatment with mercury salts) and the free keto group can be converted further, as described in paragraph 4. Finally, the thioketal function is also cleaved.

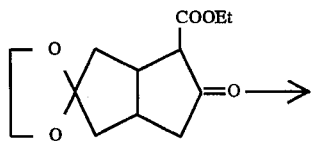

J. Chem. Soc.,
Chem. Com. 1978, 1067

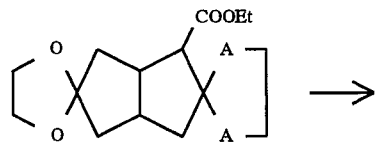

17)

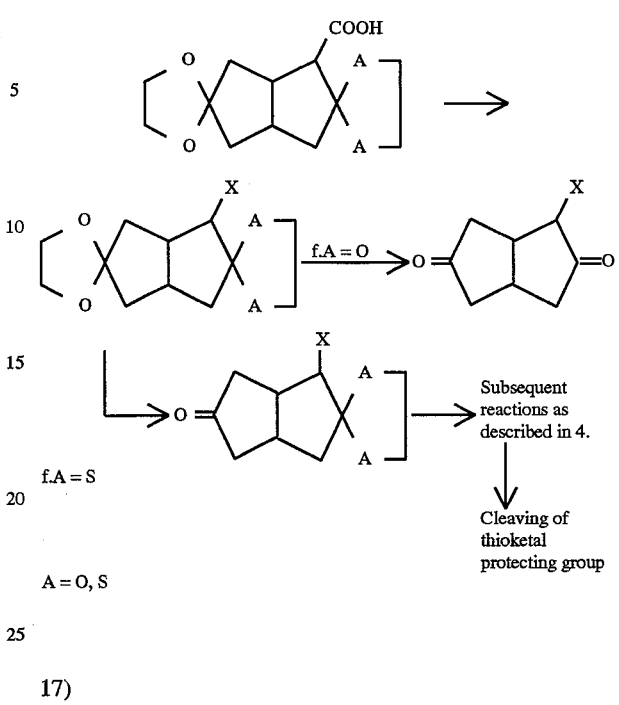

According to J. Am. Chem. Soc. 111, 6691 (1989), the esters of other bicyclo[3,3,0]octanones, bicyclo[4,3,0]nonanones and bicyclo[5,3,0]decanones are obtained, which may be partially substituted with several protected hydroxy groups and have a double bond in conjugation with the ester group. After hydrogenation of this double bond and saponification of the esters, further bicyclic carboxylic acid components are formed which can be reacted to xanthines according to the general method. Cleaving of the protecting groups by conventional methods makes it possible to release the alcohol functions.

18)

By cycloaddition of cyclopentadiene with 2-methylacrolein, crotonaldehyde or 2-methylcrotonaldehyde, substituted norbornene aldehydes are obtained and from them, in accordance with the general procedure, 8-norbornenyl-substituted xanthines. These cycloadditions may also be carried out in the presence of optically active Lewis acid catalysts (see for example J. Org. Chem. 54, 1481 (1989)) and then result in products with, in some cases, a high diastereomeric and/or enantiomeric excess. By hydrogenation of the double bond, corresponding norbornenyl derivatives are obtained, cis-dihydroxylation of the double bond with N-methylmorpholine-N-oxide/osmium tetroxide yields the corresponding cis-diols, which may be reacted further as described in paragraph 10. Epoxidation of the double bond and nucleophilic opening of the oxiran result in further substitution patterns.

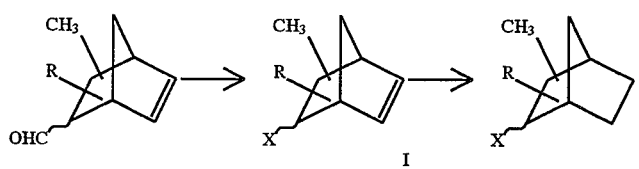

J. Org. Chem. 54, 1481 (1989)

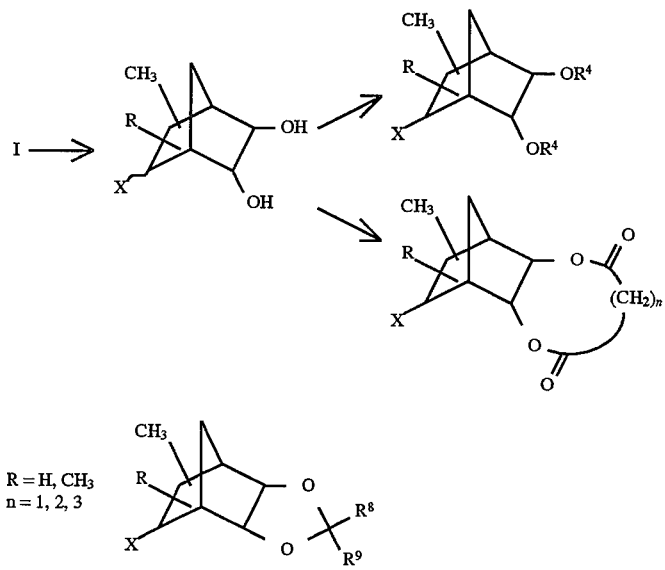

R = H, CH₃
n = 1, 2, 3

19)

From furan, by cycloaddition with acrylic acid esters using a Lewis acid as catalyst, the corresponding 2-alkoxycarbonyl-7-oxabicyclo[2,2,1]hept-5-enes can be prepared, from which xanthines can be synthesised after saponification of the ester in accordance with the general procedure. Subsequent reactions may then be carried out on the double bond as described in 19. 8-(7-oxabicyclo[2,2,1]heptan-2-yl)xanthines are expediently prepared by adopting the same procedure but hydrogenating the double bond before the saponification of the ester group.

20)

In the cycloaddition of fumaric acid dichloride with furan and basic hydrolysis of the crude product, 7-oxabicyclo[2,2,1]hept-5-en-2-endo-3-exo-dicarboxylic acid is obtained. By reacting with formic acid/hydrogen peroxide, 9-exo-hydroxy-3-oxo-2,7-dioxatricyclo[4,2,1,0$^{4,8}$]nonane-5-exo-carboxylic acid is obtained therefrom; after silylation of the alcohol function with t-butyldimethylsilyl chloride, the carboxylic acid component can be used for xanthine synthesis according to the general procedure. Cleaving of the silyl group with fluoride yields the free alcohol which can subsequently be alkylated or acylated.

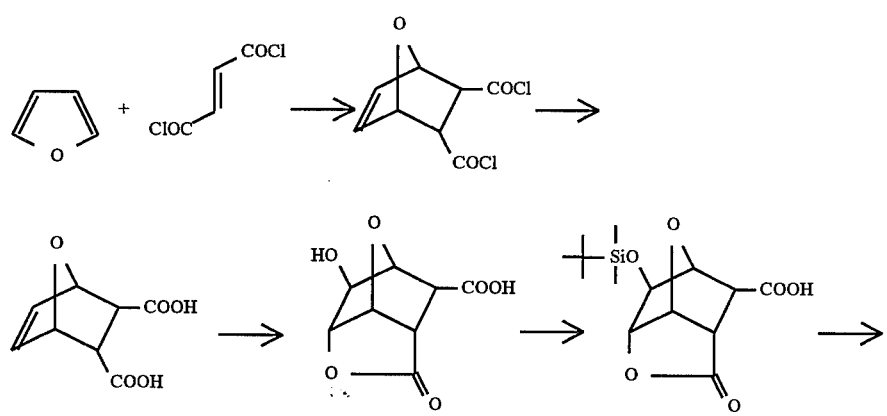

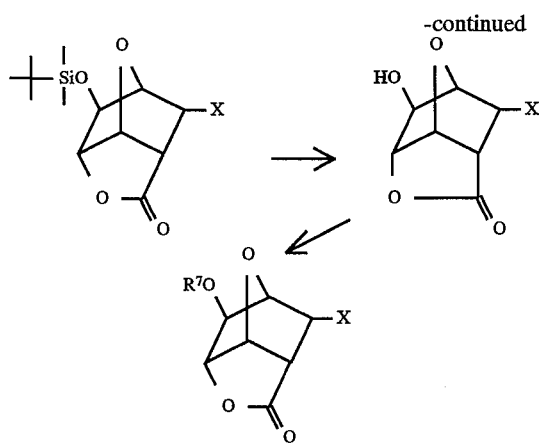
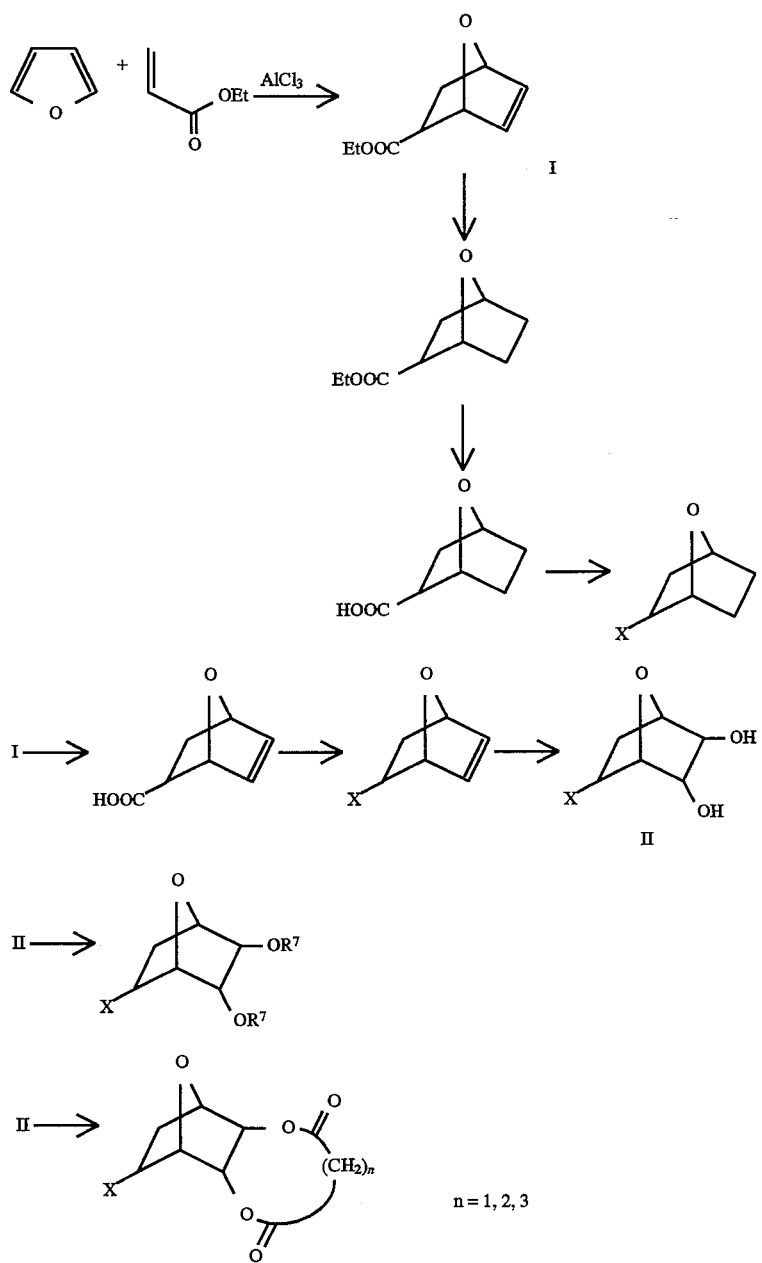
n = 1, 2, 3

EXAMPLE 1

8-(4-Morpholinyl)-1,3-dipropyl-7H-purin-2,6-dione 7.9 g (0.033 mol) of 6-amino-5-nitroso-1,3-dipropyluracil and 5.0 g (0.049 mol) of N-formylmorpholine are dissolved in 40 ml of carbon tetrachloride. At ambient temperature, 7.5 g (0.049 mol) of phosphorus oxychloride are added, the mixture is heated to reflux temperature for one hour and left to stand at ambient temperature for about 12 hours. The oil which separates off on the surface is removed, dissolved in 50 ml of dichloromethane and poured onto ice together with the remaining solution, which has been concentrated by half. After neutralisation of the aqueous phase the organic phase is separated off and the aqueous phase is extracted with dichloromethane. From the combined organic phases the title compound is obtained, after drying and evaporation, as a crystalline residue which is recrystallised from ethanol.

1.7 g (16% of theory) are obtained in the form of colourless crystals, melting point: 251°–252° C.

EXAMPLE 2

7-Benzyl-8-(3-oxocyclopentyl)-1,3-dipropylpurine-2,6-dione 10.0 g (0.031 mol) of 8-(3-oxocyclopentyl)-1,3-dipropyl-7H-purine-2,6-dione are dissolved in 30 ml of absolute dimethylformamide and after the addition of 4.6 g (0.033 mol) of potassium carbonate the mixture is stirred for 20 minutes at ambient temperature. 5.7 g (0.033 mol) of benzylbromide are added dropwise, the mixture is stirred for a further 40 minutes and the reaction is ended by the addition of water. The solution is evaporated down, the residue is taken up in water and extracted with dichloromethane. After drying and evaporation, the combined organic phases yield an oily residue which is purified on silica gel with a mixture of dichloromethane/methanol in the ratio 99:1 and then recrystallised from ethanol. 9.4 g (73.3% of theory) of the title compound are obtained in the form of colourless crystals, melting point: 145° C.

EXAMPLE 3

7-Benzyl-8-(3-(1,3-dithian-2-ylidene)-cyclopentyl)-1,3-dipropylpurine-2,6-dione

At −75° C. 14.37 ml (0.023 mol) of a 1.6M solution of butyl lithium in n-hexane is added dropwise to 4.0 g of 2-trimethylsilyl-1,3-dithiane (0.021 mol) in 15 ml of absolute tetrahydrofuran and the mixture is stirred for a further 30 minutes at −70° C. Then at the same temperature a solution of 8.0 g (0.020 mol) of 7-benzyl-8-(3-oxocyclopentyl)-1,3-dipropylpurine-2,6-dione in 70 ml of absolute tetrahydrofuran is added dropwise. The mixture is stirred for 2 hours at −70° C. and then for 2 hours at −30° C., then water is carefully added at −30° C. The phases are separated, the organic phase is evaporated down, the residue is taken up in dichloromethane, washed with water and the solution is dried and evaporated down. Purification is carried out by chromatography on silica gel using a mixture of cyclohexane/ethyl acetate as eluant in the ratio 3:1. 3.55 g (35.5% of theory) of the title compound are obtained in the form of a yellowish oil which crystallises when left to stand.

EXAMPLE 4

7-Benzyl-8-(3-methyloxycarbonyl-cyclopentyl)-1,3-dipropylpurine-2,6-dione 1.2 ml of 6N hydrochloric acid, 0.55 ml of trifluoroacetic acid and 2.38 g (8.8 mmol) of mercury(II)-chloride are successively added to a solution of 1.1 g (2.2 mol) of 7-benzyl-8-(3-(1,3-dithian-2-ylidene)-cyclopentyl)-1,3-dipropylpurine-2,6-dione in 30 ml of methanol and 6 ml of dichloromethane. The mixture is stirred for 4 hours at ambient temperature and then suction filtered over Celite. At −5° C., 90 mg of sodium borohydride are carefully added the filtrate, which is stirred for 30 minutes at 0° C., suction filtered over Celite and evaporated down. For purification the residue remaining is chromatographed on silica gel with a mixture of dichloromethane/methanol in the ratio 97:3. 0.72 g (72% of theory) of the title compound are obtained as a brownish oil.

EXAMPLE 5

8-(3-Methyloxycarbonyl-cyclopentyl)-1,3-dipropyl-7H-purine-2,6-dione 2.29 g (5.1 mmol) of 7-benzyl-8-(3-methyloxycarbonyl-cyclopentyl)-1,3-dipropylpurine-2,6-dione are hydrogenated in 40 ml of methanol with the addition of 0.5 g of dry Pearlman catalyst until the uptake of hydrogen has ceased at 20° C. under 5.0 bars. After filtering over kieselguhr the solution is evaporated down and the residue is recrystallised from isopropanol. 1.54 g (83.2% of theory) of the title compound are obtained in the form of colourless crystals, melting point 188°–194° C.

EXAMPLE 6

8-(3-Carboxycyclopentyl)-1,3-dipropyl-7H-purine-2,6-dione 1.41 g (3.9 mmol) of 8-(3-methyloxycarbonylcyclopentyl)-1,3-dipropyl-7H-purine-2,6-dione are suspended in 10 ml of ethanol and 1 ml of water, 0.77 g of potassium hydroxide are added and the mixture is refluxed for 30 minutes. After cooling to 10° C. the mixture is acidified, the crystals precipitated are suction filtered and the filtrate is extracted with dichloromethane. The combined organic extracts are dried and evaporated down; the residue is combined with the filtered crystals. In this way 1.27 g (93.4% of theory) of the title compound are obtained are beige crystals.

EXAMPLE 7

8-(3-(5-Cyanopentyl-amino-carbonyl)-cyclopentyl)-1,3-dipropyl-7H-purine-2,6-dione 0.3 g (1.9 mmol) of carbonyldiimidazole are added to a suspension of 0.67 g (1.9 mmol) of 8-(3-carboxycyclopentyl)-1,3-dipropyl-7H-purine-2,6-dione in 20 ml of dichloromethane and 1 ml of tetrahydrofuran and the mixture is stirred for 35 minutes at ambient temperature. After the addition of 0.21 g (1.9 mmol) of 6-aminocapronitrile the mixture is stirred for a further 24 hours, acidified and washed with water. The organic phase is concentrated by evaporation, the residue is taken up in 5% sodium bicarbonate solution and this solution is extracted with dichloromethane. After drying and evaporation of the organic extracts the title compound is obtained in the form of crystals which, are purified with a mixture of dichloromethane/methanol in the ratio 95:5. 0.67 g (79.8% of theory) of the title compound are obtained in the form of colourless crystals.

EXAMPLE 8

8-(3,4-cis-Dihydroxycyclopentyl)-1,3-dipropyl-7H-purine-2,6-dione

A solution of 800 mg (2.66 mmol) of 8-(3-cyclopentenyl) -1,3-dipropyl-7H-purine-2,6-dione in 200 ml of a mixture of acetone and water in the ratio 5:1 is mixed at 0° C. with 330 mg (2.76 mmol) of N-methylmorpholine-N-oxide and 2 ml of a 1% solution of osmium tetroxide in tert.-butanol. The mixture is stirred for 2 hours at 0° C., then left to warm up to ambient temperature within a period of 4 hours, after which 150 mg of sodium hydrogen sulphite, about 5 g of kieselguhr and 15 ml of water are added successively and the resulting mixture is stirred for 1 hour at ambient temperature. It is filtered to remove the solids and the acetone is distilled off. The aqueous phase is thoroughly shaken with dichloromethane, then evaporated to dryness and the residue is extracted with dichloromethane in a Soxhlet extractor. The combined organic extracts are dried and evaporated down; the residue is chromatographed on silica gel with a mixture of chloroform/methanol in the ratio 90:10 and the product is triturated with ether and then recrystallised from ethanol. 190 mg (21% of theory) of the title compound are obtained in the form of colourless crystals, melting point: 232°–233° C.

EXAMPLE 9

7-Oxo-(spiro-(cis-bicyclo[3,3,0]octane)-3,2'-1,3-dithiolane)

14.0 g (0.101 mol) of cis-bicyclo[3,3,0]octane-3,7-dione, 8.54 ml (0.101 mol) of 1,2-dimercaptoethane, 150 ml of toluene and 0.19 g of p-toluenesulphonic acid hydrate are mixed together and refluxed for 3 hours. The mixture is diluted with 140 ml of toluene, the organic phase is washed twice with 5% sodium bicarbonate solution, dried and evaporated to dryness. After chromatography with dichloromethane on silica gel, 8.8 g of di-dithioketal are isolated. Chromatography of the residual mixture with ethyl acetate and petroleum ether in the ratio 7:3 results in 1.65 g of clean starting compound as well as 5.83 g (27% of theory) of the desired mono-dithioketal in the form of yellowish crystals. A further 2.03 g of mono-dithioketal can be obtained from the di-dithioketal by treatment with mercury(II)chloride (analogously to Example 4) after purification by chromatography on silica gel with a mixture of dichloromethane and methanol in the ratio 99:1.

EXAMPLE 10

7-(1,3-Dithian-2-ylidene)-(spiro-(cis-bicyclo[3,3,0]octane)-3,2'-1,3-dithiolane)

Analogously to Example 3 5.8 g (27 mmol) of 7-oxo-(spiro-(cis-bicyclo[3,3,0]octane)-3,2'-1,3-dithiol) in tetrahydrofuran are reacted with the lithium salt of 5.39 g (28 mmol) of 2-trimethylsilyl-1,3-dithiane and 18.77 ml of a 1.6M solution of n-butyllithium in n-hexane. Purification is carried out on a silica gel-filled column using dichloromethane as eluant. The product is triturated with petroleum ether and suction filtered. 2.57 g (30% of theory) of the title compound are obtained in the form of colourless crystals.

EXAMPLE 11

7-Methyloxycarbonyl-(spiro-(cis-bicyclo[3,3,0]octane)-3,2'-1,3-diothiolane)

2.0 g (6.32 mmol) of 7-(1,3-dithian-2-ylidene)-(spiro-(cis-bicyclo[3,3,0]octane)-3,2'-1,3-dithiolane) are treated analogously to Example 4 with mercury(II)chloride. The crude product is purified on silica gel. using a mixture of dichloromethane and methanol in the ratio 99:1. In this way 1.12 g (69% of theory) of the title compound are obtained in the form of colourless crystals.

EXAMPLE 12

7-Carboxy-(spiro-(cis-bicyclo[3,3,0]octane)-3,2'-1,3-dithiolane)

1.27 g (4.9 mmol) of 7-methyloxycarbonyl-(spiro-(cis-bicyclo[3,3,0]octane)-3,2'-1,3-dithiolane) and 0.97 g (17.3 mmol) of potassium hydroxide are refluxed for 20 minutes with 1.4 ml of water and 2.8 ml of ethanol. The cooled mixture is acidified to a pH of 3, whilst cooling with ice, the crystals precipitated are suction filtered, washed with cold water and dried. 1.1 g (92% of theory) of the title compound are obtained in the form of colourless crystals.

EXAMPLE 13

8-[(Spiro-(cis-bicyclo[3,3,0]octane)-3.2'-(1.3-dithiolane))-7-yl]-1,3-dipropyl-7H-purine-2,6-dione 0.5 g (2.05 mmol) of 7-carboxy-(spiro-(cis-bicyclo[3,3,0]octane)-3,2'-(1,3-dithiolane)) and 0.32 g (2.05 mmol) of carbonyldiimidazole are stirred together with 10 ml of absolute dichloromethane for 1 hour at ambient temperature. After the addition of 0.47 g (2.05 mmol) of 5,6-diamino-1,3-dipropyluracil, the mixture is stirred for a further 4.5 hours, concentrated by evaporation and the residue is taken up in 10.3 ml of water. 0.66 g of calcium hydroxide and 3 ml of tetrahydrofuran are added and the mixture is stirred for 3 hours at 80° C. Then 7.4 ml of 50% sodium hydroxide solution are added, the mixture is stirred for a further hour at 80° C. and then left to cool. The reaction mixture is neutralised whilst being cooled with ice and then extracted with dichloromethane.

The combined organic extracts are washed with water, dried and evaporated down. They are purified by chromatography on silica gel with a mixture of dichloromethane and methanol in the ratio 95:5. 0.51 g (57% of theory) of the title compound are obtained.

EXAMPLE 14

8-(7-Oxo-cis-bicyclo[3,3,0]octan-3-yl)-1,3-dipropyl-7H-purine-2,6-dione 0.30 g (0.69 mmol) of 8-[(spiro-(cis-bicyclo-[3,3,0]octane)-3,2'-(1,3-dithiolane)-7-yl]-1,3-dipropyl-7H-purine-2,6-dione are dissolved in 7 ml of methanol and 3 ml of dichloromethane and then 0.29 ml of 6N hydrochloric acid, 0.39 g of mercury(II)chloride and 0.13 ml of trifluoroacetic acid are added successively. The mixture is stirred for 6 hours at 40° C., then another 0.43 g of mercury(II)chloride are added and the resulting mixture is stirred for 14 hours at 40° C. The suspension is suction filtered over Celite, the filter cake is washed with methanol and dichloromethane and the filtrate is mixed at 0° C. with 23 mg of sodium borohydride and stirred for 30 minutes. After refiltering through Celite, the filtrate is evaporated down and the residue is purified by chromatography on silica gel with a mixture of dichloromethane and methanol in the ratio 95:5. 230 mg (93.1% of theory) of the title compound are obtained in the form of colourless crystals, m.p. 161°–181° C. The diastereomers can be separated by chromatography with ethyl acetate. Their melting points are 162°–163° C. and 206° C. (decomposition).

EXAMPLE 15

8-(7-Hydroxy-cis-bicyclo[3,3,0]octan-3-yl)-1,3-dipropyl-7H-purine-2,6-dione 0.09 g (0.25 mmol) of 8-(7-oxo-cis-bicyclo[3,3,0]-octan-3-yl)-1,3-dipropyl-7H-purine-2,6-dione are suspended in 2 ml of ethanol and stirred for 1 hour at 0° C. after the addition of 50 mg of sodium borohydride. The mixture is evaporated down and added to 5 ml of water. The pH is adjusted to 2 and the mixture is extracted with dichloromethane. From the dried and concentrated organic extracts, a crystalline crude product is obtained which can be purified by chromatography on silica gel with a mixture of dichloromethane and methanol in the ratio 95:5. This makes it possible to separate the two isomers. They are obtained in a total yield of 80 mg (89% of theory) as colourless crystals. The polar isomer has a melting point of 230°–232° C. The non-polar isomer melts at 177°–179° C. Alternatively, the diastereomers of 8-(7-oxo-cis-bicyclo[3,3,0]octan-3-yl)-1,3-dipropyl-7H-purine-2,6-dione according to Example 14 may be reduced separately. The ketone with a melting point of 162°–163° C. then yields the alcohol with a melting point of 177°–179° C. and the ketone with a melting point of 206° yields the alcohol with a melting point of 230°–232° C.

By Mitsunobu reaction with benzoic acid (according to O. Mitsunobu, Synthesis 1981, page 1 ff) and subsequent reduction of the benzoate with lithium aluminium hydride in ether, the isomeric product with inverted alcohol configuration (m.p. 237°–239° C.) is obtained from the polar alcohol with m.p. 230°–232° C.

EXAMPLE 16

7-(1,3-Dithian-2-ylidene)-3-oxabicyclo[3,3,0[octane

At −72° C., 9.49 ml (15.14 mol) of a 6M solution of butyllithium in n-hexane is added dropwise to a solution of 2.41 ml (12.6 mmol) of 2-trimethylsilyl-1,3-dithiane in 10 ml of absolute tetrahydrofuran, the mixture is stirred for 30 minutes at −70° C. and then a solution of 1.54 g (12.17 mmol) of 7-oxo-3-oxabicyclo[3,3,0]octane in 8 ml of absolute tetrahydrofuran is added dropwise thereto. The mixture is stirred for 2.5 hours at −70° C., 1 hour at −70 to −60° C., 1.5 hours at −30° C. and 30 minutes at −30° to −10° C. After the addition of 5 ml of water the phases are separated and the organic phase is evaporated down. The residue is taken up in dichloromethane, the solution is washed with water, dried and evaporated down. The residue is purified by chromatography on silica gel with a mixture of dichloromethane and methanol in the ratio 99:1. 1.3 g (47% of theory) of the title compound are obtained in the form of colourless crystals.

EXAMPLE 17

Methyl 3-oxabicyclo[3.3.0]octane-7-carboxylate 2.15 g (9.46 mmol) of 7-(1,3-dithian-2-ylidene)-3-oxabicyclo[3.3.0]octane are treated with mercury(II)-chloride as described in Example 3. Purification is carried out by chromatography on silica gel using a mixture of dichloromethane and methanol in the ratio 97:3. 960 mg (60% of theory) of the title compound are obtained in the form of a light yellow oil.

EXAMPLE 18

3-Oxabicyclo[3.3.0]octane-7-carboxylic acid 1.06 g (6.13 mmol) of methyl 3-oxabicyclo[3.3.0]-7-carboxylate are dissolved in 1.6 ml of water and 3.2 ml of ethanol and 1.21 g (21.6 mmol) of potassium hydroxide are added. The mixture is refluxed for 30 minutes, acidified at 0° C. to a pH of 4 and extracted with dichloromethane. Drying and concentration of the combined organic extracts yields 0.62 g (65% of theory) of the title compound in the form of a crystalline product.

EXAMPLE 19

8-(3-Oxabicyclo[3.3.0]octan-7-yl)-1,3-dipropyl-7H-purine-2,6-dione was prepared in accordance with the general procedure and purified by chromatography on silica gel using a mixture of dichloromethane and methanol in the ratio 95:5 and then recrystallised from ethanol. 0.64 g (47% of theory) of the title compound are obtained in the form of colourless crystals, melting point 226°–230° C.

EXAMPLE 20

8-((1S,2R,5R)-2-Methyl-3-oxo-5-iso-propenyl-cyclopent-1-yl)-1,3-dipropyl-7H-purine-2,6-dione 1.23 g (6.8 mmol) of (1S,2R,5R)-2-methyl-3-oxo-5-isopropenyl-1-cyclopentane carboxylic acid are stirred into 35 ml of absolute dichloromethane together with 1.1 g (6.8 mmol) of carbonyldiimidazole for 1 hour at ambient temperature. 1.24 g (5.4 mmol) of 5,6-diamino-1,3-dipropyluracil are added, the solution is stirred for a further 4 hours and then evaporated down. The residue is filtered over silica gel with a mixture of dichloromethane and methanol in a ratio 95:5, the concentrated product fractions are dissolved with 0.5 ml of tetrahydrofuran and mixed with 35 ml of water. The mixture is heated to 50° C., 2.34 g of calcium hydroxide are added, the resulting mixture is stirred for 4 hours at 80° C. and left to cool. After the addition of 25.6 ml of 50% sodium hydroxide solution the mixture is acidified and extracted with dichloromethane. The organic extracts are washed with water, dried and evaporated down; the oil obtained is purified by chromatography on silica gel with a mixture of dichloromethane and methanol in the ratio 95:5. The product is triturated with ether and suction filtered.

In this way, 600 mg (49% of theory) of the title compound are obtained in the form of colourless crystals, m.p. 136°–137° C.; $[\alpha]_D^{20}$ (1% methanol)=−8.1°.

EXAMPLE 21

8-((5S)-5-endo-Methyl-bicyclo[2.2.1]hept-2-en-5-yl)-1,3-dipropyl-7H-purine-2,6-dione 2.45 g (18.0 mmol) of (5S)-5-endo-methyl-bicyclo[2.2.1]hept-2-en-5-carbaldehyde, 4.08 g (18 mmol) of 5,6-diamino-1,3-dipropyluracil, 6.5 ml of glacial acetic acid and 58 ml of absolute ethanol are stirred together for 4 hours at ambient temperature, then, after the addition of molecular sieve (0.3 nm), stirred for 3 hours at about 50° C. for approximately 12 hours at ambient temperature. 2.83 ml of diethylazodicarboxylate are then added, the mixture is stirred at ambient temperature for 1.5 hours and the reaction mixture is then suction filtered. The filtrate is concentrated by evaporation and crystallises when left to stand. The crystal slurry is triturated with methanol and suction filtered and the product is purified by chromatography on silica gel using a mixture of dichloromethane and methanol in the ratio 97:3. 2.22 g (36% of theory) of the title compound are obtained in the form of colourless crystals, melting point 133°–135° C., $[\alpha]_D^{20}$ (1%, methanol)=−30.1°. Similarly, the use of (5R)-5-endo-methyl-bicyclo[2.2.1]-hept-2-en-carbaldehyde results in the (R)-enantiomer of the title compound.

EXAMPLE 22

8-(1-Phenyl-1-cyclopentyl-1,3-dipropyl-7H-purine-2,6-dione 2.5 g (13 mmol) of 1-phenyl-cyclopentanecarboxylic acid are stirred with 2.1 g (13 mmol) of carbonyldiimidazole in 52 ml of absolute methylene chloride for 1 hour at ambient temperature. 3.0 g (13 mmol) of 5,6 -diamino-1,3-dipropyluracil are added, the solution is stirred for a further 16 hours and evaporated down. The residue is mixed with 65 ml of H₂O and 4.2 g of calcium hydroxide and stirred for 30 minutes at 80° C. 46 ml of 40% sodium hydroxide solution are added to the cooled mixture which is stirred for a further hour at 80° C. Whilst cooling with ice, the mixture is acidified to a pH of 2 and extracted with dichloromethane. The organic phase is washed with water, dried and concentrated by evaporation. It is purified over a silica gel column with a mixture of dichloromethane and methanol in the ratio 97:3 and the product is recrystallised from a mixture of isopropylether and ethanol.

600 mg (12% of theory) of the title compound are obtained in the form of colourless crystals, m.p. 164°–165° C.

EXAMPLE 23

Ethyl 7-oxabicyclo[2.2.1]hept-5-en-2-carboxylate

Under a nitrogen atmosphere and whilst cooling with ice, 10.0 g (0.147 mol) of furan are mixed at 10° to 20° C. with 6.5 g (49 mmol) of aluminium(III)chloride. The temperature is maintained at between 15° C. and 35° C., while 15.0 g (0.147 mol) of methylacrylate are added dropwise. The mixture is stirred for a further 1.5 hours at ambient temperature, water is added, whilst cooling with ice, and the mixture is extracted with dichloromethane. The organic phases are washed with water, dried and concentrated by evaporation. Purification is effected by chromatography on silica gel with a mixture of dichloromethane and methanol in the ratio 99:1 as eluant. 12.2 g (40% of theory) of the title compound are obtained in the form of a yellow oil.

EXAMPLE 24

Ethyl 7-oxabicyclo[2.2.1]heptane-2-carboxylate 5.0 g (29.7 mmol) of ethyl exo-7-oxabicyclo[2.2.1]hept-5-en-2-carboxylate are dissolved in 50 ml of ethanol and hydrogenated, with the addition of 0.5 g palladium on charcoal (5%, E10N) until the uptake of hydrogen has ceased, at 30° C. under 5 bar. The mixture is filtered and evaporated down. 4.5 g (89% of theory) of the title compound are obtained as a yellow oil.

EXAMPLE 25

7-Oxabicyclo[2.2.1]heptane-2-carboxylic acid 6.1 g (35.8 mmol) of ethyl 7-oxabicyclo[2.2.1]heptane-2-carboxylate are dissolved in 15 ml of water and 30 ml of ethanol and carefully mixed with 7.0 g (0.125 mol) of potassium hydroxide. The mixture is heated to reflux temperature for 1 hour, the ethanol is distilled off, the aqueous solution is made alkaline and extracted with dichloromethane. The organic phases are washed until neutral, dried and evaporated down.

5.0 g (98.2% of theory) of the title compound are obtained in the form of a yellow crystallising oil.

EXAMPLE 26

7-Oxabicyclo[2.2.1]hept-5-en-2-carboxylic acid 3.0 g (17.8 mmol) of ethyl 7-oxabicyclo[2.2.1]hept-5-en-2-carboxylate are suspended in 10 ml of water and 20 ml of ethanol. The temperature is kept below 20° C. by cooling with ice, while 3.5 g (62.3 mmol) of potassium hydroxide are added. The mixture is stirred for 2 hours at ambient temperature, the ethanol is distilled off at a bath temperature of 30° C. and the aqueous solution is extracted with ethyl acetate. The aqueous phase is acidified to a pH of 6 while cooling with ice and shaken with dichloromethane, then the combined organic extracts are dried and evaporated down. 0.8 g (32% of theory) of the title compound are obtained as a brown oil.

EXAMPLE 27

8-(2-exo-7-Oxabicyclo[2.2.1]heptanyl)-1,3-dipropyl-7H-purine-2,6-dione

The title compound is obtained according to the general procedure and purified by crystallising from ethanol. The title compound is obtained in the form of colourless crystals in a yield of 17% of theory, melting point 215°–216° C.

EXAMPLE 28

8-(exo-7-Oxabicyclo[2.2.1]hept-5-en-2-yl)-dipropyl-7H-purine-2,6-dione

The title compound is prepared according to the general procedure and purified by chromatography on silica gel with a mixture of dichloromethane and methanol in the ratio 99:1. It is purified once more by flash chromatography with the same eluant mixture. The product is triturated with ether and suction filtered. The title compound is obtained in the form of colourless crystals which melt at 160° C. with decomposition Intermediate compounds:

7-Benzyl-xanthines of general formula Ib as defined in claim 8 and in the synthesis plan on page 24 are important starting compounds for the preparation of pharmacologically active xanthines of formula I and are claimed as such.

General procedure for synthesising 8-substituted xanthine derivatives from 5,6-diamino-1,3-dialkyluracils and carboxylic acids:

The carboxylic acid is stirred with equimolar amounts of carbonyldiimidazole in absolute dichloromethane—optionally with the addition of absolute tetrahydrofuran—for 1 to 4 hours at ambient temperature. Then an equimolar amount of 5,6-diamino-1,3-dialkyluracil is added and the mixture is stirred for 1 to 24 hours at ambient temperature (TLC monitoring*). The mixture is evaporated down using a rotary evaporator, the residue is taken up in water and mixed with 4.5-times the molar amount of calcium hydroxide. If the suspension cannot be stirred, some tetrahydrofuran is added. The mixture is stirred at 80° C. for 1 to 6 hours, cooled and after the addition of 30-times the molar amount of 50% sodium hydroxide solution the mixture is stirred again at 80° C. until the thin layer chromatograph indicates that the amide has been totally reacted. The mixture is acidified whilst cooling with ice and extracted with dichloromethane. The combined organic extracts washed until neutral are dried and evaporated down and the product is purified by chromatography or recrystallisation.

*TLC=thin layer chromatograhy

The compounds in the following Examples may be prepared analogously to the Examples described.

List of compounds prepared
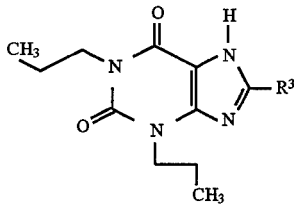
| | R³ | M.p. °C |
|---|---|---|
| 29 | 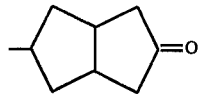 | 161–181° C. |
| | " 1st isomer | 206° C. Decomp. |
| | " 2nd isomer | 162° C. |
| 30 | 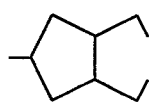 | 226–30° C. |
| 31 | 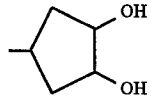 | 232–33° C. |
| 32 | 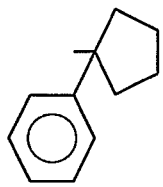 | 164–5° C. |
| 33 |  | 251–2° C. |
| 34 | 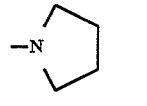 | 279–80° C. |
| 35 | 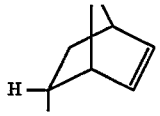 | 160° C. (Decomp.) |
| 36 | 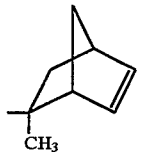 | 133–135° C., [α]$_D$ (1% MeOH) = −30.1 |
| 37 | 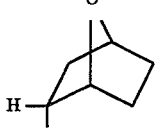 | 215–216° C. |
| 38 | 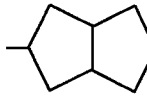 | 230–232° C. |
-continued
List of compounds prepared
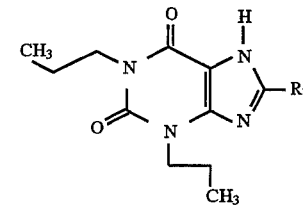
| | R³ | M.p. °C |
|---|---|---|
| | 2nd isomer | 237–239° C. |
| | 3rd isomer | 177–179° C. |
| 39 | 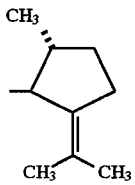 | |
| 40 | 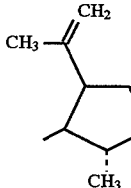 | 135–136° C. |
| 41 | 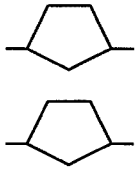 | 107° C. |
| 42 | 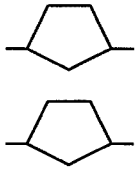 | 261° C. |
| 43 | 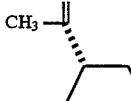 | 136–8° C. |
| 44 | 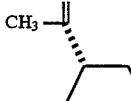 | 188–94° C. |
| 45 | 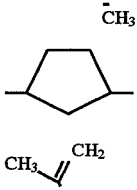 | 176–178° |
| 46 | 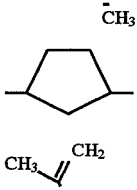 | 150–152° |

List of compounds prepared

[Structure I: 1,3-diethyl xanthine-like core with R³ substituent on imidazole]

| | R³ | M.p. °C |
|---|---|---|
| 47 | (CH₃)(CH₂=)C– cyclopentanone with CH₃ | 133–134° |
| 48 | (CH₃)₂CH– cyclopentane with CH₃, OH | 177–179° |
| 49 | gem-dimethyl cyclopentyl | 96–97° |
| 50 | norbornyl with OH, OH, O bridge | 276–278° |
| 51 | norbornenyl-CH₃ | 133–135°<br>[α]_D −30.1° |
| 52 | norbornyl-CH₃ | 138–140° |
| 53 | norbornyl with OH, OH, CH₃ | 154–156° |

List of compounds prepared

[Structure I: isomeric xanthine-like core with R³ substituent]

| | R³ | M.p. °C |
|---|---|---|
| 54 | norbornenyl-CH₃ | 127.5–128.5° |

The compounds of general formula I may be used on their own or in conjunction with other active substances according to the invention and possibly in conjunction with other pharmacologically active substances. Suitable forms include, for example, tablets, capsules, suppositories, solutions, syrups, emulsions or dispersible powders. Tablets may be produced, for example, by mixing the active substance or substances with known excipients, e.g. inert diluents such as calcium carbonate, calcium phosphate or lactose, disintegrants such as corn starch or alginic acid, binders such as starch or gelatine, lubricants such as magnesium stearate or talc and/or agents for obtaining delayed release, such as carboxymethylcellulose, cellulose acetate phthalate or polyvinylacetate. The tablets may also consist of several layers.

Coated tablets may be produced analogously by coating cores made in the same way as the tablets with substances conventionally used for tablet coatings, e.g. collidone or shellac, gum arabic, talc, titanium dioxide or sugar. In order to obtain delayed release or avoid incompatibilities, the core may also consist of several layers. Similarly, the tablet coating may consist of several layers to achieve delayed release, whilst the excipients mentioned for the tablets may be used.

Syrups containing the active substances or combinations of active substances according to the invention may additionally contain a sweetener such as saccharin, cyclamate, glycerol or sugar as well as a flavour enhancer, e.g. a flavouring such as vanillin or orange extract. They may also contain suspension adjuvants or thickeners such as sodium carboxymethylcellulose, wetting agents, e.g. condensation products of fatty alcohols with ethylene oxide or preservatives such as p-hydroxybenzoates.

Injectable solutions are produced in the usual way, e.g. by adding preservatives such as p-hydroxybenzoates or stabilisers such as alkali metal salts of ethylene diamine tetraacetic acid, and are then transferred into injection vials or ampoules.

Capsules containing one or more active substances or combinations of active substances may be prepared for example by mixing the active substances with inert carriers such as lactose or sorbitol and encapsulating them in gelatine capsules.

Suitable suppositories may be produced for example by mixing with carriers provided for this purpose, such as neutral fats or polyethyleneglycol or derivatives thereof.

The Examples which follow illustrate the invention without restricting its scope:

Examples of pharmaceutical formulations

| A) Tablets | per tablet |
|---|---|
| Active substance | 100 mg |
| Lactose | 140 mg |
| Corn starch | 240 mg |
| Polyvinylpyrrolidone | 15 mg |
| Magnesium stearate | 5 mg |
| | 500 mg |

The finely ground active substance, lactose and some of the corn starch are mixed together. The mixture is screened, after which it is moistened with a solution of polyvinylpyrrolidone in water, kneaded, moist granulated and dried. The granules, the remaining corn starch and the magnesium stearate are screened and mixed together. The mixture is compressed to form tablets of suitable shape and size.

| B) Tablets | per tablet |
|---|---|
| Active substance | 80 mg |
| Corn starch | 190 mg |
| Lactose | 55 mg |
| Microcrystalline cellulose | 35 mg |
| Polyvinylpyrrolidone | 15 mg |
| Sodium carboxymethyl starch | 23 mg |
| Magnesium stearate | 2 mg |
| | 400 mg |

The finely ground active substance, some of the corn starch, lactose, microcrystalline cellulose and polyvinylpyrrolidone are mixed together, the mixture is screened and processed with the remaining corn starch and water to form granules which are dried and screened. The sodium carboxymethyl starch and magnesium stearate are added thereto and mixed and the mixture is compressed to form tablets of suitable size.

We claim:

1. A xanthine derivative of formula I wherein $R^1$ is $C_{1-6}$-alkyl, $C_{3-4}$-alkenyl or $C_{3-4}$-alkynyl;

$R^2$ is $C_{1-6}$-alkyl, $C_{3-4}$-alkenyl or $C_{3-4}$-alkynyl;

$R^3$ represents a group of formula wherein $R^a$ may represent H, or $C_1$–$C_4$ alkyl, and $R^b$ may represent H, or $C_1$–$C_4$ alkyl, or $R^3$ represents a group of formula wherein A=O, S; n,m=0,1,2,3 or 4 and n+m=2,3 or 4 and one of the two rings may be mono- or polysubstituted by $OR^4$, $C_{1-6}$-alkyl, $C_{3-6}$-alkenyl, $C_{3-6}$-alkynyl, $C_{1-4}$-alkylidene, phenyl, substituted phenyl, optionally substituted aralkyl, $NR^5R^6$, $COOR^4$, $CONR^5R^6$, $OR^4$, $SR^4$, $OR^7$, —$(CH_2)_{1-4}$—$NR^5R^6$,—$(CH_2)_{1-4}CONR^5R^6$, $C_{1-4}$-alkyl-S—$R^4$, $C_{1-4}$-alkyl-$OR^4$, =O, $C_{1-4}$-alkyl-$OR^7$, $C_{1-4}$-alkyl-$COOR^4$, $NHR^7$, optionally substituted $C_{3-6}$-cycloalkyl, or $R^3$ represents a group of formula wherein A=$CH_2$; n,m=0,1,2,3 or 4 and n+m=2,3 or 4 and one of the two rings is mono- or polysubstituted by $OR^4$, $C_{1-6}$-alkyl, $C_{3-6}$-alkenyl, $C_{3-6}$-alkynyl, $C_{1-4}$-alkylidene, phenyl, substituted phenyl, optionally substituted aralkyl, $NR^5R^6$, $COOR^4$, $CONR^5R^6$, $OR^4$, $SR^4$, $OR^7$, —$(CH_2)_{1-4}$—$NR^5R^6$, —$(CH_2)_{1-4}CONR^5R^6$, $C_{1-4}$-alkyl-S—$R^4$, $C_{1-4}$-alkyl-$OR^4$, =O, $C_{1-4}$-alkyl-$OR^7$, $C_{1-4}$-alkyl-$COOR^4$, $NHR^7$, optionally substituted $C_{3-6}$-cycloalkyl, or $R^3$ represents a group of formula with A=O or —$CH_2$—$CH_2$—, whilst the ring system is optionally substituted by one or more $C_{1-6}$-alkyl, $C_{2-6}$-alkenyl, $C_{2-6}$-alkynyl, $NR^5R^6$, $COOR^4$, $CONR^5R^6$, $OR^4$, $OR^7$, $SR^4$, =O, $CH_2OR^4$, $CH_2OR^7$, $CH_2COOR^4$, $CH_2CONR^5R^6$;

$R^4$ represents hydrogen, $C_{1-8}$-alkyl, optionally substituted $C_{3-6}$-cloalkyl, optionally substituted $C_{1-4}$-alkylphenyl, $C_{3-6}$-alkenyl, optionally substituted aralkyl;

$R^5$ represents hydrogen, a $C_{1-6}$-alkyl group, optionally substituted $C_{3-6}$-cycloalkyl, optionally substituted aralkyl;

$R^6$ represents hydrogen, a $C_{1-6}$-alkyl group, optionally substituted aralkyl, a group of general formula —$(CH_2)_n$—$NR^5R^6$ (where $R^5$ may be the same or different), —$(CH_2)_n$—CN, —$(CH_2)_n$—$OR^4$, —$(CH_2)_n$—$OR^7$, —$(CH_2)_n$—$NHR^7$ wherein n=2,3,4,5,6,7 or 8, or $R^5$ and $R^6$ together form an optionally substituted five, six- or seven-membered ring which may contain a further heteroatom from the group comprising oxygen, sulphur or nitrogen, whilst the nitrogen atom may be substituted by the group $R^4$;

$R^7$ represents an amino acid group, linked via the carbonyl function, of a naturally occuring amino acid, CO—$C_{1-13}$-alkyl, optionally substituted CO—$C_{1-13}$-alkylphenyl;

in the form of a racemate, an optically active compound, a pure diastereomer or mixture of diastereomers or a pharmacologically acceptable acid addition salt thereof.

2. A xanthine derivative of formula I

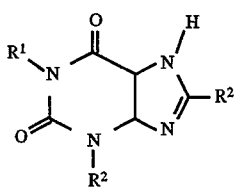

wherein $R^1$ represents a $C_{3-4}$-alkyl group, a propenyl group or a propargyl group;

$R^2$ represents a $C_{3-4}$-alkyl group, a propenyl group or a propargyl group;

$R^3$ represents a group of formula

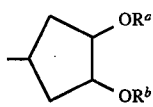

wherein $R^a$ may represent H, or $C_1$–$C_4$ alkyl, and
$R^b$ may represent H, or $C_1$–$C_4$ alkyl, or $R^3$ represents a group of formula

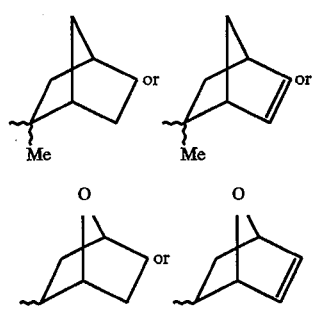

optionally substituted by $CH_3$, OH or $OR^7$; or $R^3$ represents a oxa- or thiabicyclo[3.3.0]octane, optionally substituted by $OR^4$, =O, $OR^7$;

$R^3$ represents a bicyclo[3.3.0]octane, substituted by $OR^4$, =O, $OR^7$;

$R^4$ represents hydrogen, a $C_{1-3}$-alkyl group, benzyl;

$R^5$ represents hydrogen, $C_{1-3}$-alkyl group;

$R^6$ represents hydrogen, methyl, ethyl, propyl, —$(CH_2)_n$—$NH_2$, —$(CH_2)_n$—CN, —$(CH_2)_n$—$OR^4$, —$(CH_2)_n$—$OR^7$, —$(CH_2)_n$—$NR^5R^5$, —$(CH_2)_n$—$NHR^7$ (wherein n=2 through 8);

$R^7$ represents prolinoyl, CO—$(CH_2)_{0-3}$—$CH_3$ or benzoyl, in the form of a racemate, an optically active compound, a pure diastereomer or mixture of diastereomers or a pharmacologically acceptable acid addition salt thereof.

3. A xanthine derivative of formula

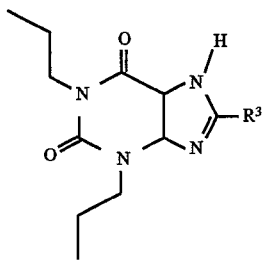

wherein $R^3$ represents a group of formula

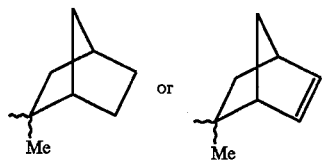

in the form of a racemate, an optically active compound, a pure diastereomer or mixture of diastereomers or a pharmacologically acceptable acid addition salt thereof.

4. A xanthine derivative of formula

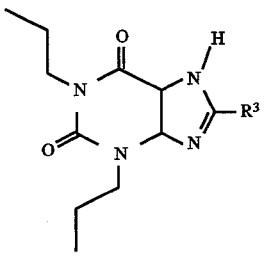

wherein $R^3$ represents a bicyclo[3.3.0]octane, substituted by OH, =O;

$R^3$ represent a oxabicyclo[3.3.0]octane, optionally substituted by OH, =O;

in the form of a racemate, an optically active compound, a pure diastereomer or mixture of diastereomers or a pharmacologically acceptable acid addition salt thereof.

5. A xanthine derivative of formula

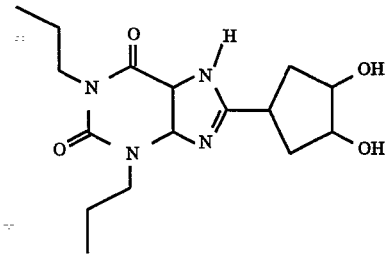

in the form of a racemate, an optically active compound, a pure diastereomer or mixture of diastereomers or a pharmacologically acceptable acid addition salt thereof.

6. A pharmaceutical composition of matter comprising a xanthine derivative as recited in claim 1,2,3,4 and 5.

7. A pharmaceutical composition of matter comprising a xanthine derivative as recited in claim 2 and a pharmaceutically acceptable carrier or excipient.

8. A pharmaceutical composition of matter comprising a xanthine derivative as recited in claim 8 and a pharmaceutically acceptable carrier or excipient.

9. A method of treating disease in a warm-blooded animal receptive to adenosine antagonists which comprises administering to said animal a therapeutically effective mount of a xanthine derivative as recited in claim 1,2,3,4 and 5.

10. A method of treating disease in a warm-blooded animal receptive to adenosine antagonists which comprises administering to said animal a therapeutically effective amount of a xanthine derivative as recited in claim 2.

11. A method of treating disease in a warm-blooded animal receptive to adenosine antagonists which comprises administering to said animal a therapeutically effective amount of a xanthine derivatives as recited in claim 3.

* * * * *